US006453333B1

(12) United States Patent
Glynias et al.

(10) Patent No.: US 6,453,333 B1
(45) Date of Patent: **\*Sep. 17, 2002**

(54) RESEARCH SYSTEM USING MULTI-PLATFORM OBJECT ORIENTED PROGRAM LANGUAGE FOR PROVIDING OBJECTS AT RUNTIME FOR CREATING AND MANIPULATING BIOLOGICAL OR CHEMICAL DATA TO FACILITATE RESEARCH

(75) Inventors: Manuel J. Glynias, Westlake; Daniel A. Forsch, Cleveland Heights; Michael C. Dickson, Berea; Joanne M. O'Dell, Sagamore Hills; Michal S. Soclof, Beachwood, all of OH (US)

(73) Assignee: LION Bioscience AG, Heidelberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/095,083

(22) Filed: Jun. 10, 1998

Related U.S. Application Data

(63) Continuation-in-part of application No. 08/873,217, filed on Jun. 11, 1997, now Pat. No. 6,125,383.

(51) Int. Cl.[7] ............................................. G06F 13/00
(52) U.S. Cl. ................. 709/202; 709/203; 709/218
(58) Field of Search ................. 709/202, 201, 709/203, 217, 218, 315, 219; 707/3; 717/10

(56) References Cited

U.S. PATENT DOCUMENTS

| | | | |
|---|---|---|---|
| 5,329,619 A | | 7/1994 | Page et al. |
| 5,386,552 A | | 1/1995 | Garney |
| 5,450,583 A | * | 9/1995 | Inada .......................... 709/315 |
| 5,457,797 A | | 10/1995 | Butterworth et al. |
| 5,473,777 A | | 12/1995 | Moeller et al. |
| 5,491,820 A | * | 2/1996 | Belove et al. .................. 707/3 |
| 5,517,645 A | | 5/1996 | Stutz et al. |
| 5,539,909 A | | 7/1996 | Tanaka et al. |
| 5,544,302 A | | 8/1996 | Nguyen |
| 5,557,518 A | | 9/1996 | Rosen |
| 5,581,760 A | | 12/1996 | Atkinson et al. |
| 5,608,900 A | | 3/1997 | Dockter et al. |
| 5,613,148 A | | 3/1997 | Bezviner et al. |
| 5,778,368 A | | 7/1998 | Hogan et al. |
| 5,781,732 A | | 7/1998 | Adams |
| 5,854,750 A | | 12/1998 | Phillips et al. |
| 6,044,224 A | * | 3/2000 | Radia et al. ................... 717/10 |
| 6,223,217 B1 | * | 4/2001 | Pettus ......................... 709/219 |

OTHER PUBLICATIONS

Orfali et al. "The Essential Distributed Objects Survival Guide", 1996, pp. 248–249.*
PCT Search Report for International Patent Application No. PCT/US98/11981 dated Oct. 26, 1998.
Evans E et al: "Using Java applets and Corba for multi-user distributed applications" IEEE Internet Computing, May–Jun. 1997, IEEEm USA, vol. 1, No. 3, pp. 43–55.
NetGenics—Press Releases, Jun. 9, 1997, pp. 1–9.
Duan N N: "Distributed database access in a corporate environment using Java" Computer Networks and ISDN Systems, vol. 28, n. 11, May 1996, pp. 1149–1156.
Achard F et al: "Ubiquitous distributed objects with CORBA" Pacific Symposium on Biocomputing '97, Proceedings of the Pacific Symposium Biocomputing '97, Maul, HI, USA, Jan. 6–9, 1997, pp. 39–50.

* cited by examiner

*Primary Examiner*—Le Hien Luu
(74) *Attorney, Agent, or Firm*—Amin & Turocy, LLP

(57) ABSTRACT

A drug discovery research system which includes a plurality of computers. The drug discovery research system provides for at least one of the plurality of computers to run a multi-platform object oriented programming code, and at least one of the plurality of computers to store drug discovery related data. The system has a network architecture interconnecting the plurality of computers. The network architecture allows objects to transparently communicate with each other. The drug discovery research system provides for integrating and organizing data to facilitate drug discovery research.

14 Claims, 13 Drawing Sheets

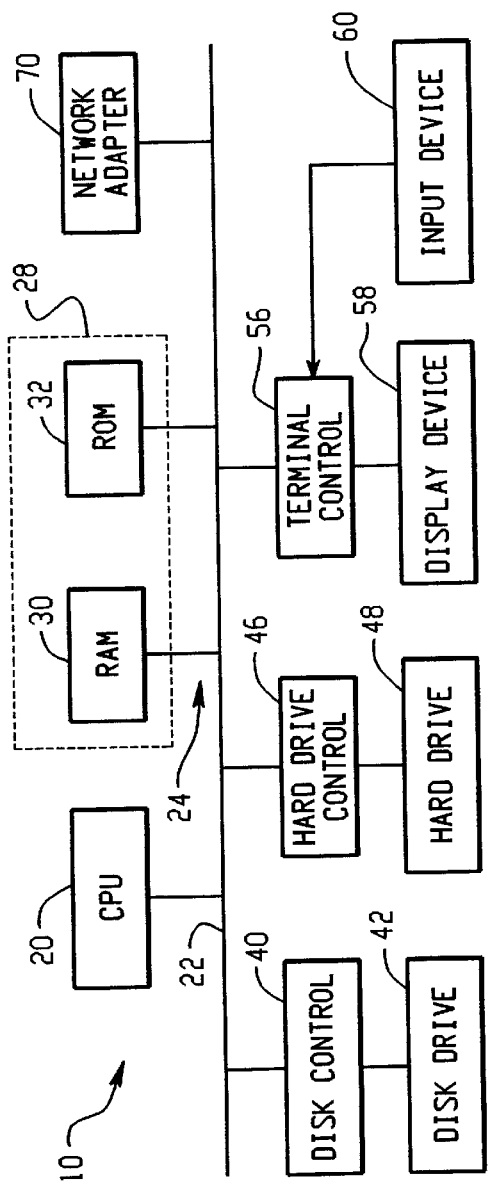
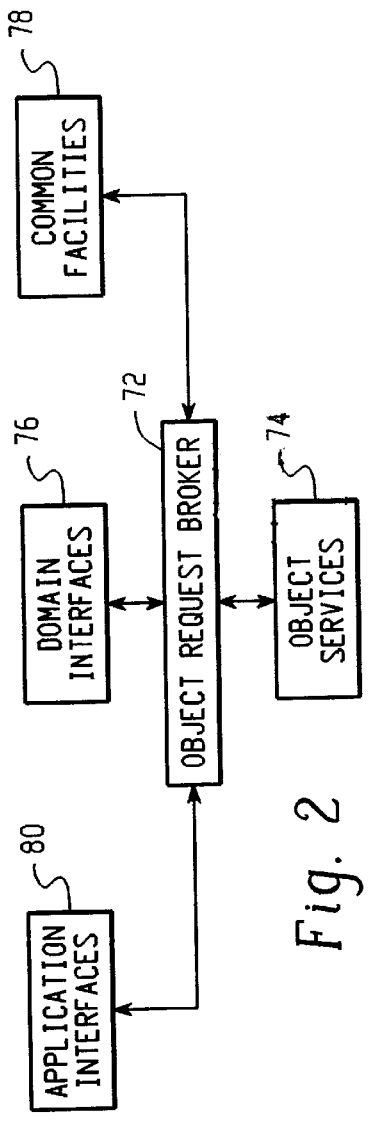

| | | | | |
|---|---|---|---|---|
| Sequence | Features | Map | Description | Analyses |
| Name: Goose ME | Length: 1673 bp | Selection: 74 to 276 | | |
| ☐ Upper Case ☑ Double Stranded | ☐ Rna | ☐ Show Annotations | | |

```
10RPB                                                                        60RPL
atgaagggg  gctacgaggt  gctccgcgac  cctcacctca  acaagggat  ggcattacc    60
tactctccc  cgatgctcca  cgaggcgctg  gggagtggagt  tgttcccta  ccgtaaatgg ttggaggga  ggcaacaact  gaatattcat  ggactatgc   caccttgctt  tctcggtcaa  120
aacctcctct  ccgttgttga  ctatataagta  cctgataacg gtggaacgaa  agagccagtt gatgtccagg  ttttcagtat  tcttaagaat  tttgaaagac  tgacaccgac  ctagacagat  180
ctacaggtcc  aaaagtcata  agaattctta  aaacttctg   actgtggctg  gatctgtcta acattctact  aatgagtctt  caggatcgaa  atgaaaagct  cttctataaa  gtgctgactt  240
tgtaagatga  ttactcaga   gtcctagctt  tactttcga   gaagatatt   cacgactgaa ctgacataga  aaggttcatg  cctatgtttt  atactcccac  tgtgggactg  gcttgccagc  300
gactgtatct  ttccaagtac  ggataacaaa  tatgagggtg  acacctgac   cgaacggtcg aatatggttt  agcatttcgg  aggccaagag  gacttttat   tactatccat  gaccggggac  360
ttataccaaa  tcgtaaagcc  tccggttctc  ctgaaaata   atgataggta  ctggccctg acatcgctac  aatgctcaag  tcctggccag  aaagtgtcat  caaggctatt  gtggtgacag  420
tgtagcgatg  ttacgagttc  aggaccggtc  tttcacagta  gttccgataa  cacccactgtc atggagaacg  tattcttggt  cttggagacc  tcggctgcta  tggcatgggc  atcccggttg  480
tacctcttgc  ataagaacca  gaacctctgg  agccgacgat  accgtacccg  tagggccaac
```

Fig. 7a

RESEARCH SYSTEM USING MULTI-PLATFORM OBJECT ORIENTED PROGRAM LANGUAGE FOR PROVIDING OBJECTS AT RUNTIME FOR CREATING AND MANIPULATING BIOLOGICAL OR CHEMICAL DATA TO FACILITATE RESEARCH

CROSS-REFERENCE TO RELATED APPLICATIONS

This application is a continuation-in-part of co-pending U.S. patent application Ser. No. 08/873,217 filed Jun. 11, 1997, U.S. Pat. No. 6,125,383, by Manuel Glynias et al. and titled SYSTEM FOR FACILITATING DRUG DISCOVERY DATA. The entire disclosure of which is incorporated by reference.

TECHNICAL FIELD

The present invention relates generally to a client/server based collaborative system which allows for the integration of problem specific objects, algorithms and analyses. In particular, the present invention relates to a system which integrates and organizes biological and/or chemical data to facilitate drug discovery and design.

BACKGROUND OF THE INVENTION

The use of computers for retrieval and analysis of data has become the standard in information-intensive industries such as finance and the sciences. As bodies of information have grown and become distributed into databases, a new set of disciplines (Informatics) aimed at studying the context of this data has been created.

Pharmaceutical and biotechnology companies place a high value on DNA and protein sequence information. For example, in 1996 a major pharmaceutical company earned revenues of $38 million based on subscription fees for the use of its sequence databases. Many pharmaceutical companies have large contracts and/or investments with gene discovery companies. However, since an unanalyzed DNA sequence has limited value, the outcome of gene discovery often hinges on bioinformatics—the application of computer technology to the analysis and management of sequence data.

Computer technology is essential to analyzing data such as DNA sequences, but today users of informatics related software find themselves in a dilemma. On one hand, the complexity of information makes the presentation of results crucial to understanding so the best informatics programs make use of interactive, graphical presentations. The best environment for understanding complex data relationships is a desktop computer running a graphical interface, but the computational demands of DNA sequence analysis require powerful workstations, or supercomputers. Such (often very expensive) computers do not support interactive graphical representations of analyses. At present there is no single program that performs all of the functions necessary for successfully analyzing DNA and protein sequences.

Although Web (e.g., network) technology allows users at a desktop computer to access programs and databases on remote computers, such programs lack a unifying standard. In particular, these programs have their own unique interface—program specific format for input and output. Ease of use is sacrificed, since users must learn to operate many different programs and must jump formidable technical hurdles to exchange data between these programs. As this often involves laborious and tedious manipulation of data files as well as detailed knowledge of the operations of programs and the quirks of each operating system, the chances of error are significant. Currently, scientists either spend unnecessary hours to accomplish tasks with these tools, or simply choose not to try, and potentially miss important observations.

In addition, web technology does not permit sufficient interactions between programs and databases. When a new program or database becomes available, the program or database needs to be first integrated and organized into each computer wishing to assess such new program or database before interactions between any old program or database with the new program or database is permissible. Each program or database originally installed on the computers needs to be told the addition of the new program or database in order to effectively utilize the new program or database. This could potentially be time consuming and costly.

In industrial fields, there are additional information management issues. Oftentimes, several researchers working in different offices in different states or countries have a need to share data results of tests and findings to maximize efficiency. Data management and analysis software, to date, has failed to fulfill this important need set, leaving the user to communicate his findings via post, E-mail, or informal verbal communication.

These situations particularly exist in such fields as bio-informatics and chemi-informatics, where users have a strong need for sophisticated manipulation of data, with interactive and accessible output. Additionally, these users have an identifiable need for real-time sharing of pertinent information across multi-functional teams.

One answer to this dilemma is the use of a client/server system, (e.g. software on a personal computer or workstation, running a graphical user interface (GUI), acting as a client of server software running on larger, faster machines). Data is stored on central machines, allowing easy access for everyone on a project team. However, for such a system to function smoothly, the clients and the servers must share communication protocols, so either the software developer must control both the client and server software or a common standard must be adopted. While client-server solutions have become increasingly popular, traditional client/server systems are deficient in several ways which have made them unsuitable as an effective software support for a rapidly changing field like drug discovery.

Conventional client/server systems tend to suffer from inherent inflexibility, due to the tight coupling of the client and server. To operate properly, the client software must "know" on what particular computer the server software runs, and the protocol with which to "talk" to the server. If the server machine is busy or down, the client software is unable to work, even if other machines are available that could process its request. Such software is not very "soft", as too many decisions are hardwired to it. If well designed, such systems can handle existing needs, but often need to be scrapped and totally rewritten if business needs change. In a rapidly changing field like bioinformatics, for example, the useful life of such software might be measured in months. Conventional client/server systems are, in addition, often very difficult to maintain and upgrade, since any changes made to the server requires complementary changes to the client. This situation is known as the "fat client" problem. For example, in a system that may have hundreds or even thousands of clients, even the slightest improvement in the server may lead to an enormous task for the system administrator in updating the improvement among the clients.

Furthermore, researchers in industry face significant security issues. Sequence data (that may have cost millions of dollars to collect) cannot be sent over the extremely public Internet where anyone might be listening. Consequently, many useful tools for sequence analysis (e.g., those provided over the Internet by the National Center for Biotechnology Information (NCBI), such as BLAST or Entrez) may be undesirable to use for researchers in industry due to the lack of security.

Drug discovery includes an almost parallel situation as mentioned above with respect to chemical data. Like Bioinformatics, there is no system currently available in the area of chemi-informatics which facilitates drug discovery without encountering many of the aforementioned deficiencies of conventional systems.

Thus, in light of the above problems associated with client/server systems and their applicability to Bioinformatics, Chemi-informatics and other data intensive industries, there is a strong need in the art for a system that overcomes these problems. In particular, there is a strong need for a system that provides for integrating and organizing biological and/or chemical data in order to facilitate drug discovery and design. Moreover, there is a strong need for a system that provides for a secure research environment that can be used by researchers in industry.

SUMMARY OF THE INVENTION

The present invention relates to a client/server based collaborative system which allows for the integration of problem specific objects, algorithms and analyses. The subject invention allows for sharing these objects, analyses and algorithms among a plurality of application programs. This includes a display function (workstation client), serviced by the server, capable of executing procedures without writing the program codes and properties in the application codes of each client. The present invention further provides for implementing this framework under object-class centric security, in order to provide access controls for the objects. The present invention also provides for a client/server interface in which both the client and the server are implementation language-neutral and architecture-independent. As a result, the present invention provides for a system which integrates and organizes biological and/or chemical data to facilitate drug discovery and design.

The present invention functions, according to one specific example, to integrate the object-calling and cooperation methods of a Common Object Request Broker Architecture (CORBA)-based system with dynamic creation and manipulation of new objects, through object-class inheritance, and graphical representation of these objects. The present invention facilitates dynamic object creation through "just in time" communication of correct object classes from the server to the client and the client to the server (e.g., remote method invocation). The present invention further facilitates dynamic access by the client to software applications that are resident on the server. Thus, the present invention presents a dual model which allows clients access in the absence of permanently-loaded software ("zero-footprint" application access), to software applications residing on the server.

According to one aspect of the invention, a research system is provided. The research system includes at least two computers, including a first computer and a second computer. The first computer runs a multi-platform object oriented programming code and stores vertical market specific data. The research system also includes a network architecture which operatively couples the at least two computers, the network architecture allowing objects to transparently communicate with each other and affording the second computer access to the object oriented programming code and the vertical market specific data. The research system provides for integrating and organizing the vertical market specific data to facilitate research.

According to another aspect of the invention a research system is provided. The research system includes at least two computers, including a first computer and a second computer. The first computer runs a multi-platform object oriented programming code and the second computer stores vertical market specific data. The research system additionally includes a network architecture which operatively couples the at least two computers. The network architecture allows objects to transparently communicate with each other and affords the first computer access to the vertical market specific data and the second computer access to the object oriented programming code. The research system provides for integrating and organizing the vertical market specific data to facilitate research.

According to still another aspect of the present invention a research system is provided. The research system includes a plurality of computers, wherein at least one of the plurality of computers runs a multi-platform object oriented programming code and another of the plurality of computers stores at least one of vertical market specific data and biological data. The research system includes means for interconnecting the plurality of computers such that objects transparently communicate with one another; and means for integrating the at least one of vertical market specific data and biological data to facilitate research.

According to yet another particular aspect of the present invention, a research system is provided, including: at least two computers, including a first computer and a second computer, the first computer running a multi-platform object oriented programming code and storing vertical market specific data and analyses (both herein referred to as objects), a second computer acting as a client to the first computer; and a network architecture interconnecting the at least two computers, the network architecture allowing objects to transparently communicate with each other via transactions or protocols; wherein the research system provides for integrating and organizing the vertical market specific data to facilitate research.

According to another aspect of the present invention, a bioinformatics research system is provided, including: a plurality of computers, at least one of the plurality of computers running a multi-platform object oriented programming code, and at least one of the plurality of computers storing biological data, and at least one of the plurality of computers acting as a client to one or more servers, with any of the plurality of computers assuming any of a plurality of functions dynamically; and a network architecture interconnecting the plurality of computers, the network architecture allowing objects to transparently communicate with each other via transactions or protocols; wherein the bioinformatics research system provides for integrating and organizing the biological data to facilitate biological research.

Another aspect of the present invention provides for a research system, including: a plurality of computers, at least one of the computers being operative as a server for the research system; wherein the system instantiates Java client classes by name at run time to implement CORBA client interfaces to changing server components.

In accordance with yet another aspect of the present invention a chemi-informatics research system is provided, including: a plurality of computers, at least one of the plurality of computers running a multi-platform object oriented programming code, and at least one of the plurality of computers storing chemical data and at least one of the computers acting as a client to one or more servers, with any of the plurality of computers assuming any of a plurality of functions dynamically; and a network architecture interconnecting the plurality of computers, the network architecture allowing objects to transparently communicate with each other via transactions or protocols; wherein the chemi-informatics research system provides for integrating and organizing the chemical data to facilitate chemical research.

Still yet another aspect of the invention provides for an informatics research system including a server computer for carrying out operations in connection with the system, the server computer being operatively coupled to a network backbone. The research system also includes at least one client computer for providing user access to the informatics research system, the at least one client computer being operatively coupled to the network backbone; wherein the client computer has dynamic, "zero footprint" access to a plurality of software applications and informatics data via the server computer.

In accordance with another aspect of the invention, a method to perform informatics based research is provided. In the method, a first computer is used to run a multi-platform object oriented programming code, the first computer being operatively coupled to a network backbone. A second computer having stored thereon vertical market specific data is also used, the second computer being operatively coupled to the network backbone. A network architecture is employed to network the first and second computers to form a research system, the research system allowing objects to transparently communicate with each other, wherein the first computer has dynamic, "zero-footprint" access to the vertical market specific data residing on the second computer. The method further includes the step of using the research system to integrate and organize the vertical market specific data to facilitate research.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 1 is a block diagram of a computer system in accordance with the present invention;

FIG. 2 is a block diagram of a Common Object Request Broker Architecture (CORBA);

FIG. 7a is a drawing of a screen view for viewing DNA sequence data in accordance with the present invention;

DETAILED DESCRIPTION OF THE INVENTION

Figure 3:
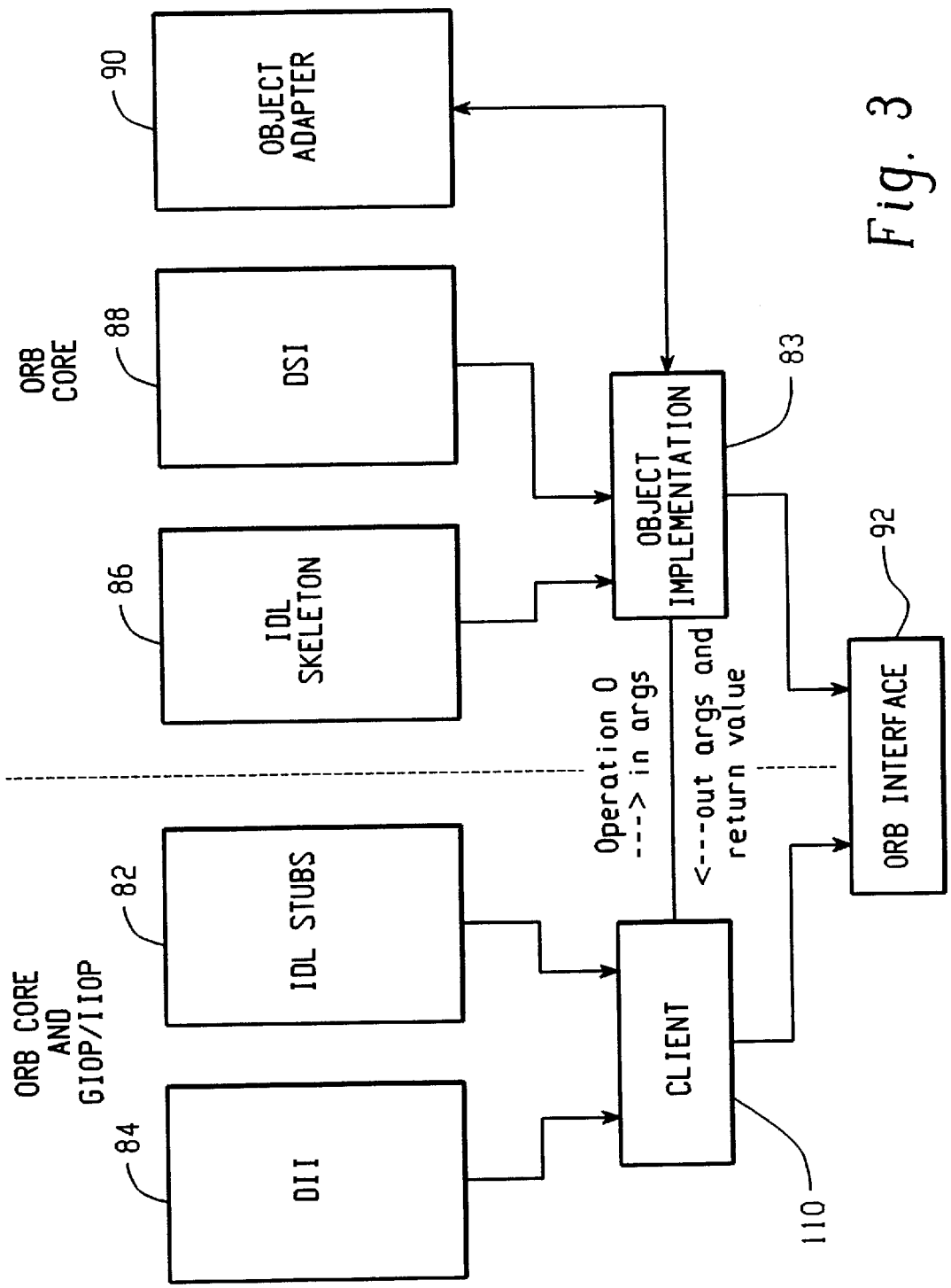
FIG. 3 is a block diagram of a CORBA ORB architecture.

The present invention will now be described with reference to the drawings, wherein like reference numerals are used to refer to like elements throughout.

As will be readily apparent from the discussion herein, the present invention provides a novel approach to bioinformatics and/or chemi-informatics by employing a system based on a graphically-rich, cross-platform, zero-footprint client for the analysis of DNA and protein sequences. The aforementioned client-server problems are overcome through the integration of object oriented protocols and Java for a graphical user interface. The present invention provides for creating an environment for team computing that provides for controlled access to shared data, automatic notification of new or modified data, an integrated task management system, and a full history of every change made on the project. The present invention overcomes the problems of interacting with multiple databases and tools in order to perform bioinformatics and chemi-informatics research by integrating and organizing database searches and data analyses and returning the results from the searches in a single, graphically-rich view. Furthermore, the present invention affords for increased data security by providing server-based storage of data behind a firewall and/or employing encrypted analyses.

Referring initially to FIG. 1, a detailed block diagram of a computer system 10 is shown in accordance with the present invention. This system may be employed as either a client and/or a server in accordance with the present invention. The computer system 10 includes a central processing unit (CPU) 20 which is coupled to a bus 22. The CPU or processor 20 can be any of a plurality of processors, such as the Pentium, Pentium II, Pentium MMX, Pentium Merced, Power PC, SPARC, SGI_MIPS and other similar and compatible processors. It will be appreciated that since the present invention provides for a multiplatform environment as described in greater detail below, most major processors and/or computers may be employed to carry out the present invention. The processor 20 functions to perform various operations described herein as well as for carrying out other operations related to the system 10. The manner in which the processor 20 can be programmed to carry out the functions relating to the present invention will be readily apparent to those having ordinary skill in the art based on the description provided herein.

The bus 22 includes a plurality of signal lines 24 for conveying addresses, data and controls between the CPU 20 and a number of other system bus components. The other system bus components include a memory 28 (including a Random Access Memory (RAM) 30 and a Read Only Memory (ROM) 32) and a plurality of input/output (I/O) devices. The memory 28 serves as data storage and may store appropriate operating code to be executed by the processor 20 for carrying out the functions described herein.

The RAM 30 provides program instruction storage and working memory for the CPU 20. The ROM 32 contains software instructions known as the Basic Input/Output System (BIOS) for performing interface operations with the I/O devices. Also stored in the ROM 32 is a software routine which operates to load a boot program from the booting device. The boot program will typically be executed when the computer system 10 is powered on or when initialization of the system 10 is needed.

The I/O devices include basic devices such as data storage devices (e.g., floppy disks, tape drives, CD ROMs, hard disks). Typically, the I/O devices communicate with the CPU 20 by generating interrupts. The CPU 20 distinguishes interrupts from among the I/O devices through individual interrupt codes assigned thereto. Responses of the CPU 20 to the I/O device interrupts differ, depending, among other things, on the devices generating the interrupts. Interrupt vectors are provided to direct the CPU 20 to different interrupt handling routines.

The interrupt vectors are generated during initialization (e.g., boot up) of the computer system 10 by execution of the BIOS. Because responses of the CPU 20 to device interrupts may need to be changed from time to time, the interrupt vectors may need to be modified from time to time in order to direct the CPU 20 to different interrupt handling routines. To allow for modification of the interrupt vectors, they are stored in the RAM 30 during operation of the computer system 10.

A disk control subsystem 40 bidirectionally couples one or more disk drives 42 (e.g., floppy disk drives, CD-ROM drives, etc.) to the system bus 22. The disk drive 42 works in conjunction with a removable storage medium such as a floppy diskette or CD-ROM.

A hard drive control subsystem 46 bidirectionally couples a rotating fixed disk, or hard drive 48 to the system bus 22. The hard drive control subsystem 46 and hard drive 48 provide mass storage for CPU instructions and data.

A terminal control subsystem 56 is also coupled to the bus 22 and provides output to a display device 58, typically a CRT monitor, and receives inputs from a manual input device 60 such as a keyboard. Manual input may also be provided from a pointing device such as a mouse.

A network adapter 70 is provided for coupling the system 10 to a network.

One of the preferred implementations of the present invention is as several sets of instructions in a code module resident in the main memory (e.g., RAM 30). Until required by the computer system 100 (FIG. 4), the sets of instructions may be stored in another computer memory, for example, in a hard disk drive, or in a removable memory such as an optical disk for eventual use in a CDROM or a floppy disk for eventual use in the floppy disk drive.

In the preferred embodiment, the present invention is implemented via object oriented programming techniques. Object oriented programming shifts the emphasis of software development away from function decomposition and towards the recognition of units of software called "objects" which encapsulate both data and functions. Object Oriented Programming (OOP) objects are software entities comprising data structures and operations on data. Together, these elements enable objects to model virtually any real-world entity in terms of its characteristics, represented by its data elements, and its behavior represented by its data manipulation functions. In this way, objects can model concrete things like people and computers, and they can model abstract concepts like numbers or geometrical concepts. For example, an "object-oriented" biotechnologist would be mostly concerned with the DNA strand he/she is designing, and secondarily with the tools used to make it—a "non-object-oriented" biotechnologist would think primarily of his tools.

The benefit of object technology arises out of three basic principles: encapsulation, polymorphism and inheritance.

Objects hide or encapsulate the internal structure of their data and the algorithms by which their functions work. Instead of exposing these implementation details, objects present interfaces that represent their abstractions cleanly with no extraneous information. Polymorphism takes encapsulation one step further—the idea being many shapes, one interface. A software component can make a request of another component without knowing exactly what that component is. The component that receives the request interprets it and figures out according to its variables and data how to execute the request. The third principle is inheritance, which allows developers to reuse pre-existing design and code. This capability allows developers to avoid creating software from scratch. Rather, through inheritance, developers derive subclasses that inherit behaviors which the developer then customizes to meet particular needs.

In particular, an object includes, and is characterized by, a set of data (e.g., attributes) and a set of operations (e.g., methods), that can operate on the data. Generally, an object's data is ideally changed only through the operation of the object's methods. Methods in an object are invoked by passing a message to the object (e.g., message passing). The message specifies a method name and an argument list. When the object receives the message, code associated with the named method is executed with the formal parameters of the method bound to the corresponding values in the argument list. Methods and message passing in OOP are analogous to procedures and procedure calls in procedure-oriented software environments.

However, while procedures operate to modify and return passed parameters, methods operate to modify the internal state of the associated objects (by modifying the data contained therein). The combination of data and methods in objects is called encapsulation. Encapsulation provides for the state of an object to only be changed by well-defined methods associated with the object. When the behavior of an object is confined to such well-defined locations and interfaces, changes (e.g., code modifications) in the object will have minimal impact on the other objects and elements in the system.

Each object is an instance of some class. A class includes a set of data attributes plus a set of allowable operations (e.g., methods) on the data attributes. As mentioned above, OOP supports inheritance—a class (called a subclass) may be derived from another class (called a base class, parent class, etc.), where the subclass inherits the data attributes and methods of the base class. The subclass may specialize the base class by adding code which overrides the data and/or methods of the base class, or which adds new data attributes and methods. Thus, inheritance represents a mechanism by which abstractions are made increasingly concrete as subclasses are created for greater levels of specialization.

The use of object oriented programming provides for a framework approach to bioinformatics and chemi-informatics application development. The present invention employs abstract classes, which are designs of sets of objects that collaborate to carry out a set of responsibilities. Frameworks are essentially groups of interconnected objects and classes that provide a prefabricated structure for a working application.

Accordingly, a user interface framework in accordance with the present invention may provide the support and default behavior of bioinformatics and/or chemi-informatics user windows, tool bars, command bars, etc. By basing the framework on object oriented technology, the behavior can be inherited and overridden to allow developers to extend the framework and create customized solutions in the bioinformatics and/or chemi-informatics research arena. As a result, significant advantages are achieved over employing conventional programming techniques used in the bioinformatics and/or chemi-informatics area since a programmer is not required to change original code but rather to extend from existing code. Moreover, the developers no longer have to work blindly through layers of code because the framework provides architectural guidance and modeling and also frees the programmers to supply specific actions unique to the bioinformatics and/or chemi-informatics problem domain.

According to an exemplary embodiment of the present invention, Java and CORBA (Common Object Request Broker Architecture) are employed to carry out the present invention. Java is an object-oriented, distributed, secure, architecture neutral language. Java provides for object-oriented design which facilitates the clean definition of interfaces and makes it possible to provide reusable "software ICs." Java has an extensive library of routines for copying easily with TCP/IP protocols like HTTP and FTP. Java applications can open and access objects across a network via URLs with the same ease to which programmers are accustomed to accessing a local file system.

Furthermore, Java utilizes "references" in place of a pointer model and so eliminates the possibility of overwriting memory and corrupting data. Instead of pointer arithmetic that is employed in many conventional systems, the Java "virtual machine" mediates access to Java objects (attributes and methods) in a type-safe way. In addition, it is not possible to turn an arbitrary integer into a reference by casting (as would be the case in C and C++ programs). In so doing, Java enables the construction of virus-free, tamper-free systems. The changes to the semantics of references make it virtually impossible for applications to forge access to data structures or to access private data in objects that they do not have access to. As a result, most activities of viruses are precluded from corrupting a Java system. Thus, the present invention provides for a substantially securer environment in which to carry out drug discovery related research.

Java affords for the support of applications on networks. Networks are composed of a variety of systems with a variety of CPU and operating system architectures. To enable a Java application to execute anywhere on the network, a compiler generates an architecture neutral object file format—the compiled code is executable on many processors, given the presence of the Java runtime system. Thus, Java is useful not only for networks but also for single system software distribution. In the present personal computer market, application writers have to produce versions of their applications that are compatible with the IBM PC and with the Apple Macintosh. However, with Java, the same version of the application runs on all platforms. The Java compiler accomplishes this by generating bytecode instructions which have nothing to do with a particular computer architecture. Rather, they are designed to be both easy to interpret on any machine and easily translated into native machine code on the fly.

Being architecture neutral, the "implementation dependent" aspects of the system are reduced or eliminated. The Java virtual machine (VM) can execute Java bytecodes directly on any machine to which the VM has been ported. Since linking is a more incremental and lightweight process, the development process can be much more rapid and exploratory. As part of the bytecode stream, more compile-time information is carried over and available at runtime.

Thus, the use of Java in the present invention provides a server to send bioinformatics and/or chemi-informatics programs over the network as easily as traditional servers send data. These programs can display and manipulate data, such as DNA sequences on a client computer. The present invention through the use of Java supports execution on multiple platforms. That is the same bioinformatics and/or chemi-informatics programs can be run on substantially all computers—the same Java program can work on a Macintosh, a Windows 95 machine, a Sun workstation, etc. To effect such multi-platform support, a network connection adapter 70 and a network browser (not shown) such as Netscape Navigator or Microsoft Internet Explorer may be used in at least one embodiment of the present invention. It should be appreciated, however, that a Java stand-alone application may be constructed to achieve a substantially equivalent result. Although the present invention is described with respect to employing Java, it will be appreciated that any suitable programming language may be employed to carry out the present invention.

The present invention instantiates Java client classes by name at run time to implement CORBA client interfaces to changing server components. That is the present invention integrates the Java programming to communicate with services distributed on various computers on the intranet through the use of CORBA technology, which is discussed in greater detail below.

Using this technology, a given bioinformatics and/or chemi-informatics task can be performed by the computer most optimally suited for it, and these decisions can be made dynamically. For example, if a given computer that provides a service is busy or down, the system will find an alternate source for that service, and provide it to the client immediately. The combination of Java-based client software and CORBA-based distributed services leads to a client/server system that facilitates bioinformatics and/or chemi-informatics researching substantially.

Most current and past object oriented programming (OOP) systems are restricted to utilizing and making calls to objects within the same address space as the process utilizing or calling the objects. That is, a process cannot typically access objects located within other processes including where those other processes are located on the same or different host computers. However, distributed OOP systems allow processes to access objects located in remote address spaces located in the same or other host systems. A standard for such distributed OOP systems currently exists called Common Object Request Broker Architecture (CORBA) and is described in The Common Object Request Broker: Architecture and Specification, published by the Object Management Group (OMG), which is hereby incorporated by reference. This architecture allows a process to make calls to objects in other address spaces typically by constructing the necessary communication paths during compilation.

In simple terms, CORBA allows applications to interact and communicate closely at a higher level of abstraction than merely sending packets of data back and forth. Applications in a heterogeneous computing environment can interact without worries of how the two different machines and operating systems can interface. Thus, CORBA specifies a system which provides interoperability between objects in a heterogeneous distributed environment and in a way transparent to the programmer.

FIG. 2 illustrates the primary components in the OMG reference model. An Object Request Broker (ORB) is shown generally at reference numeral 72 and is discussed in greater detail below. Tied to the ORB 72 are the object services 74 which are domain-independent interfaces that are used by many distributed object programs. For example, a service providing for the discovery of other available services is almost always necessary regardless of the application domain. For instance the object services may provide a naming service which allows clients 110 (FIG. 4) to find objects based on names, and/or a trading service which allows clients to find objects based on their properties.

Also tied to the ORB 72 are domain interfaces 76 which are interfaces oriented toward specific application domains. Common facilities 78 are core interfaces that are oriented toward facilitating the construction of end-user applications. Application interfaces 80 are developed specifically for a given application.

The Object Request Broker (ORB) 72 is a key component of CORBA. It acts as the agent between computers, between a client application and the data source server application, between vertical market technologies sitting on the same or different computers, and between specially wrapped CORBA objects. It encompasses all of the communication infrastructure necessary to identify and locate objects, handle connection management and deliver data. In general, the ORB 72 is not required to be a single component; it is simply defined by its interfaces. The ORB 72 is a significant part of CORBA; it is responsible for the communication of requests. The ORB 72 can help the client locate and establish communications between the two end-points. Depending upon the implementation, the two end-points might even be communicating with different transport protocols with the ORB 72 acting as a gateway between the two. Each end-point has an interface definition that all ORBs can interact with. This end-point interface is created using the Interface Definition Language (IDL) as specified by CORBA.

Turning now to FIG. 3 the basic functionality provided by the ORB 72 consists of passing the requests from clients 110 to the object implementations 83 on which they are invoked. Object implementations define operations that implement a CORBA IDL interface. As will be appreciated, object implementations can be written in a variety of languages including (but not limited to) C, C++, Java, Smalltalk, and Ada.

The ORB 72 provides a mechanism for transparently communicating client requests to target object implementations. The ORB 72 simplifies distributed programming by decoupling the client from the details of method invocations. This makes client requests appear to be local procedure calls. When the client 110 (which, in this and all of the proceeding examples may indicate either a generic client or a "workstation client" employing a user interface) invokes an operation, the ORB 72 is responsible for finding the object implementation, transparently activating it if necessary, delivering the request to the object, and returning any response to the client 110. In order to make a request, the client 110 can communicate with the ORB Core through the IDL stub 82 or through the Dynamic Invocation Interface (DII) 84. CORBA IDL stubs and skeletons serve as the "glue" between the client and server applications, respectively, and the ORB 72. DII 84 allows the client 110 to directly access the underlying request mechanisms provided by the ORB 72. The stub 82 represents the mapping between the language of implementation of the client and the ORB core. Thus, the client request can be written in any language as long as the implementation of the ORB 72 supports this mapping.

The ORB Core then transfers the request to the object implementation which receives the request as an up-call through either an IDL skeleton 86, or a dynamic skeleton interface (DSI) 88. The DSI 88 is the server side's analogue to the client side's DII 84. The DSI 88 allows the ORB 72 to deliver requests to an object implementation that does not statically define the type of the object it is implementing. The Object Adapter 90 assists the ORB with delivering requests and with activating the object. The ORB interface 92 is a logical entity that may be implemented to decouple applications from implementation details. This interface 92 provides for converting object references to strings and vice versa, and creating argument lists for requests made through the DII 84 described above.

The present invention incorporation of Java and CORBA provides for organizing and integrating bioinformatics and/or chemi-informatics data sources and analytical engines. Analysis tools and databases are integrated into the system through the creation of "wrappers". The creation of "wrappers" is well known to those skilled in the art, and therefore detailed discussion related thereto to such is eliminated for sake of brevity. In short, a wrapper is a small program that encapsulates the knowledge of each server program's requirements, its inputs and output formats, and its quirks. Unlike conventional systems, the present invention frees the user from the burden of learning how to operate many different programs. Since the inputs and outputs of the wrapper are in a common format, all of the data sources and analytical engines available on substantially any server, including legacy or preexisting systems, can be made to intercommunicate.

The system is described in its preferred embodiment here herein, and its specific interactions will be described in more detail later in this document. In general, this invention consists of a client-server based collaborative system, which may be delivered across a Local Area Network (LAN) or Wide-Area Network (WAN) for distribution of objects in the vertical domain.

Figure 4:
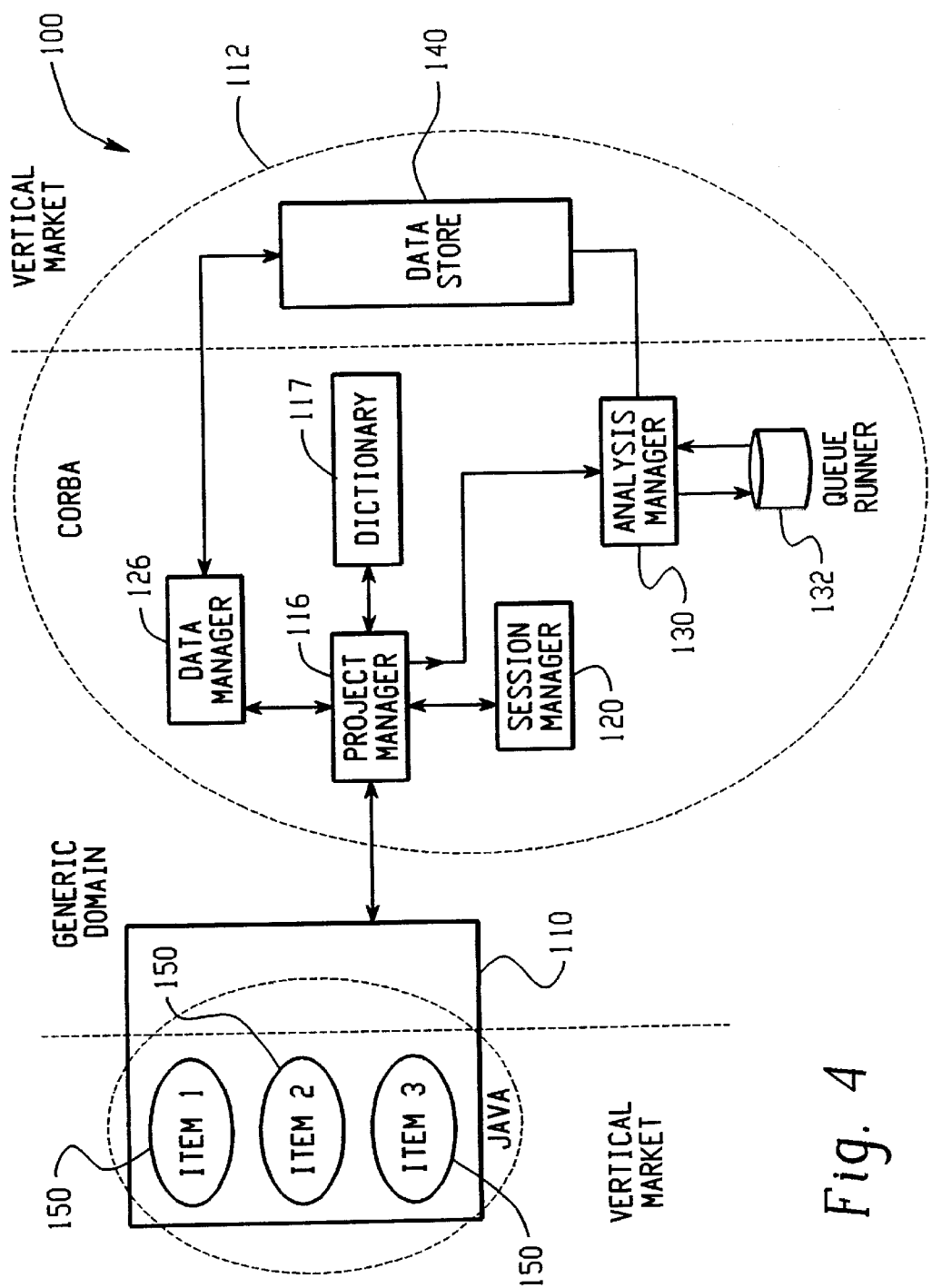
FIG. 4 is a block diagram of a drug delivery research system in accordance with the present invention.

FIG. 4 is a drawing of a preferred system 100 in accordance with the present invention. The system 100 consists of a plurality of clients 110 (only one client 110 is shown for ease of understanding) connected to a main server 112 shown in phantom. It will be appreciated that the clients 110 may serve as sub-servers, respectively, with respect to various projects, data items, etc. Furthermore, the system 100 may include a plurality of servers 112. However, for ease of understanding the present system will be described with one client 110 connected to one main server 112.

The system 100 may be divided into generic and vertical domains, where generic domains relate to non-specific markets and vertical domains relate to specific markets.

The server 112 includes a project manager 116 which the client 110 is tied to. The project manager 116 is responsible for controlling the system 100 in accordance with the present invention. The project manager 116 is coupled to a dictionary 117 which maintains a list of those items which the project manager 116 is capable of managing and/or creating. A session manager 120 coupled to the project manager 116 provides a user account database and authentication service. Also tied to the project manager 116 are a data manager 126 and an analysis manager 130. The data manager 126 serves to control and access data of the system 100 which may be requested by clients 110 via the project manager 116. The analysis manager 130 provides for controlling and accessing any of the various analysis tools available to the system 100 for performing analyses on the data of the system 100. The analysis manager 130 is also coupled to a queue runner 132. The queue runner 132 maintains background execution of analyses on behalf of the analysis manager 130.

Both the data manager 126 and the analysis manager 130 are coupled to a datastore 140 as are the project manager 116 and session manager 120. The datastore 140 houses much of the data (including analyses results) of the system 100. In the preferred embodiment the datastore 140 houses object oriented data as well as non-object oriented data. The datastore 140 may be partitioned in order to maximize the efficient storage of data thereon. For example, general data may be partitioned in a different section of memory than analyses routines which are used to run analyses on the general data.

The client 110 includes object stubs (e.g., DNA sequence item) 150 which represent views of data that reside on the server 112. For example a DNA sequence object stub that resides on the workstation client 110 is a view (in Java) that knows how to display a DNA sequence. The DNA sequence item does not possess the physical data of the particular DNA sequence until it is requested. Rather the DNA sequence item contains a set of methods that provide for rendering the DNA sequence on the screen 58 (FIG. 1) from data (on the server side located at the datastore 140) which represents the DNA sequence. Thus, the DNA sequence item 150 provides for drawing the DNA sequence on the screen 58 by manipulating data that resides on the server 112. The client 110 simply stores a temporary cached copy of the DNA data.

If there is ever a change at the server end with respect to a persistent copy of data of a particular item that is currently being viewed by a client 110, the server 112 sends a callback to the client 110 informing the client 110 that it is viewing an obsolete version of the data. The server 112 then instructs the client 110 to refresh its contents with respect to that data item and to re-render it on the screen 58. Thus the client 110 serves as a view manager of persistent data residing on the server 112. The client 110 is notified when state changes occur, and the client 110 in response refreshes its cached memory to reflect the state change.

Figure 5C:
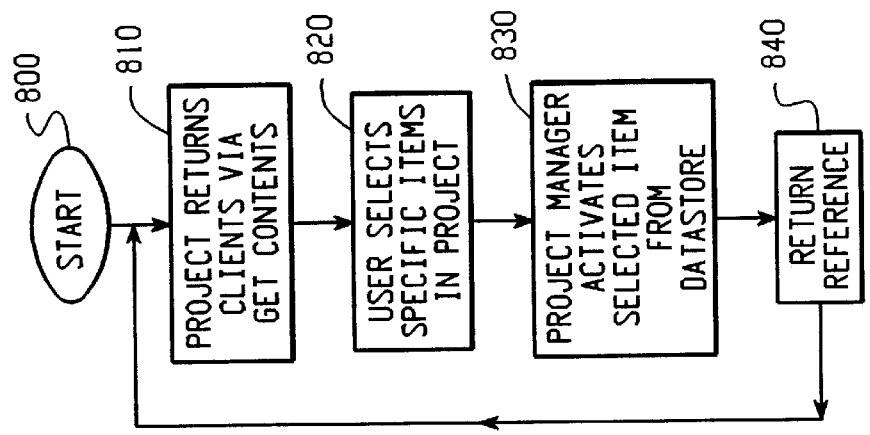
FIG. 5c is a server-view flowchart for accessing and updating a system designed in accordance with the present invention.
Figure 5B:
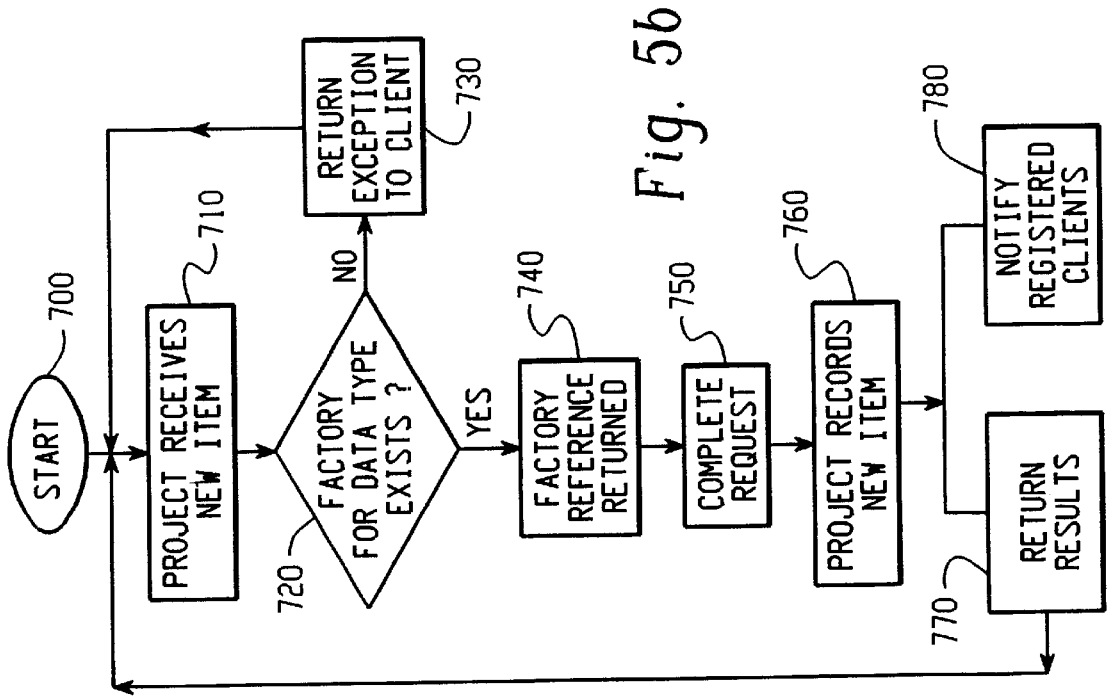
FIG. 5b is a server-view flowchart for updating specific data objects in a system designed in accordance with the present invention.
Figure 5A:
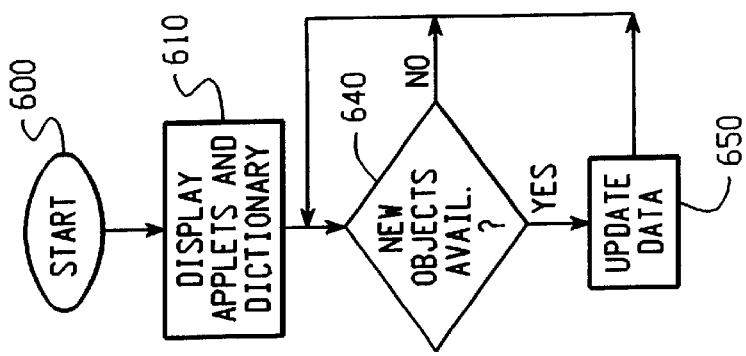
FIG. 5a is a client-view flowchart for accessing a system designed in accordance with the present invention.

Accessing and updating the system 100 designed in accordance with the present invention can be easily understood from the flowcharts shown in FIG. 5a, FIG. 5b, and FIG. 5c. Turning initially to FIG. 5a, a client-view flowchart of the operations of a system 100 designed in accordance with the present invention is shown. Beginning in step 600, a program (designed in accordance with the present invention) at the client's site is accessed, and initial communication is established between the client 110 and the server 112. Such initializations create "just in time" communication with the server 112, and basic code required to perform any user's command is downloaded. The dictionary 117 or a list containing all of the things the project manager 116 knows how to manage or create is also available for the user to access after the initial communication with the server 112 in step 600. Due to the "just in time" communication feature, minimal code is required to reside at the client's site, as is discussed in greater detail below. In step 610, the display device 58 at the client's site displays the Java programs downloaded from the initial communication established in step 600 with the server 112. The user then may also choose to display the dictionary 117 using the client interface. In addition, each Java program can issue commands to the server 112 and receive results back from the server 112 individually.

The ability to access objects whether analyses, data types (hereinafter referred to as items), or collections (such as databases) is by the object's interface name, and these interface names, which are simple strings, are registered in the dictionary 117, which can be accessed by the workstation client. When a new object factory, analysis or collection is registered, the name is added and integrated into the dictionary 117, and is immediately available for the clients 110 to review and utilize. Every time a new object is created or an existing object is accessed, Java classes which allow viewing and accessing of the object are downloaded. Creation of such viewers as part of the overall object oriented programming is conventionally known and is not further discussed for sake of brevity. The dictionary 117 is discussed in greater detail below.

It will be apparent to those having ordinary skill in the art from the description provided herein to understand that a command by the user can generate a new object. For example, an 'add' command could result in importing a new sequence object to a collection or to a project. However, since the command is not carried out on the client side, but instead is sent by the client 110 to the server 112 and carried out on the server side, the new object is actually generated by the server 112 on the server side. Thus, the new object will be automatically registered with the project manager 116 as discussed in greater detail in connection with FIG. 5b.

Referring back to FIG. 5a, independent from commands issued by the user, the processor 20 concurrently executes step 640. In step 640, the processor 20 determines if the server 112 has sent a callback to the client 110 informing the client 110 that it is viewing an obsolete version of the data. A callback could result from a variety of processes. For example, a new object may have been registered with the dictionary 117 after the workstation client downloads the dictionary 117. Other workstation clients using a related program may have created a new item such as a DNA sequence. Other manners in which the server 112 will issue a callback should be readily apparent to those having ordinary skill in the art based on the description provided herein and are not further discussed for sake of brevity.

If a callback from the server 112 has been received by the client 110, the processor 20 proceeds to step 650 and refreshes its contents with respect to that data item and to re-display it on the screen 58. The processor 20 then returns to step 640. If no callbacks from the server 112 have been received by the client 110, after completing step 640, the processor 120 also returns to step 620 and determines if a new callback has been received from the server 112.

Because the communication between the client 110 and the server 112 is inter-coupled and the proxy stubs implemented on the client 110 complement the skeleton on the server 112, the server 112 responds on behalf of the client 110. In other words the server 112 behaves as an interpreter and understands what the clients request and delivers the results thereto.

Referring now to FIG. 5b, when the server processor 20 initiates, the processor 20 does not attempt to establish communication with any clients 110. Beginning in step 700, the server processor 20 starts power-on and general initializations as part of the overall initializations of a system 100 in accordance with the present invention. Such initializations (e.g., virus check) are conventionally known and are not further discussed for sake of brevity.

In the case of the creation of a new data item, the client 110 contacts the project manager 116 with a request for a new data item which is received by the project manager 116 in step 710. Next the project manager 116 in step 720 consults a list of available object factories to determine if the object factory requested is available. If no factory is located, the project manager 116 proceeds to step 730 where an exception 730 is returned to the client 110 indicating the server 112 cannot complete the new item request. Following step 730, the project manager 116 returns to step 710. If in step 720 a factory is located the project manager 116 proceeds to step 740 where a factory reference is returned to the project manager 116. Next in step 750 the object factory completes the request from the client 110. In step 760 the project manager 116 records the new item creation. The project manager 116 then returns the results, in the form of an object reference to the client 110 in step 770, and notifies all other registered interested clients 110 that a new data object has been created in step 780. Following step 770, the project manager returns to step 710.

Referring now to FIG. 5c, there is shown a situation in which the client 110 desires to call a method on, or otherwise modify a data object. More particularly, beginning at step 800 the client 110 contacts the project manager 116, which returns in step 810 an updated list of project contents to all registered clients 110. Next in step 820 the client selects a specific object in a project. Following step 820 the project manager 116 in step 830 activates the selected object from the datastore 140. Finally, in step 840 the project manager 116 returns a data reference to the client 110 and the process is returned to step 810.

Multiple clients may perform the steps outlined above in parallel, and further the project manager 116 may also implement various "housekeeping functions", independent from the operation of specific client requests.

The invention as described may be applied to specific examples of bioinformatics and chemi-informatics as described below.

Figure 6A:
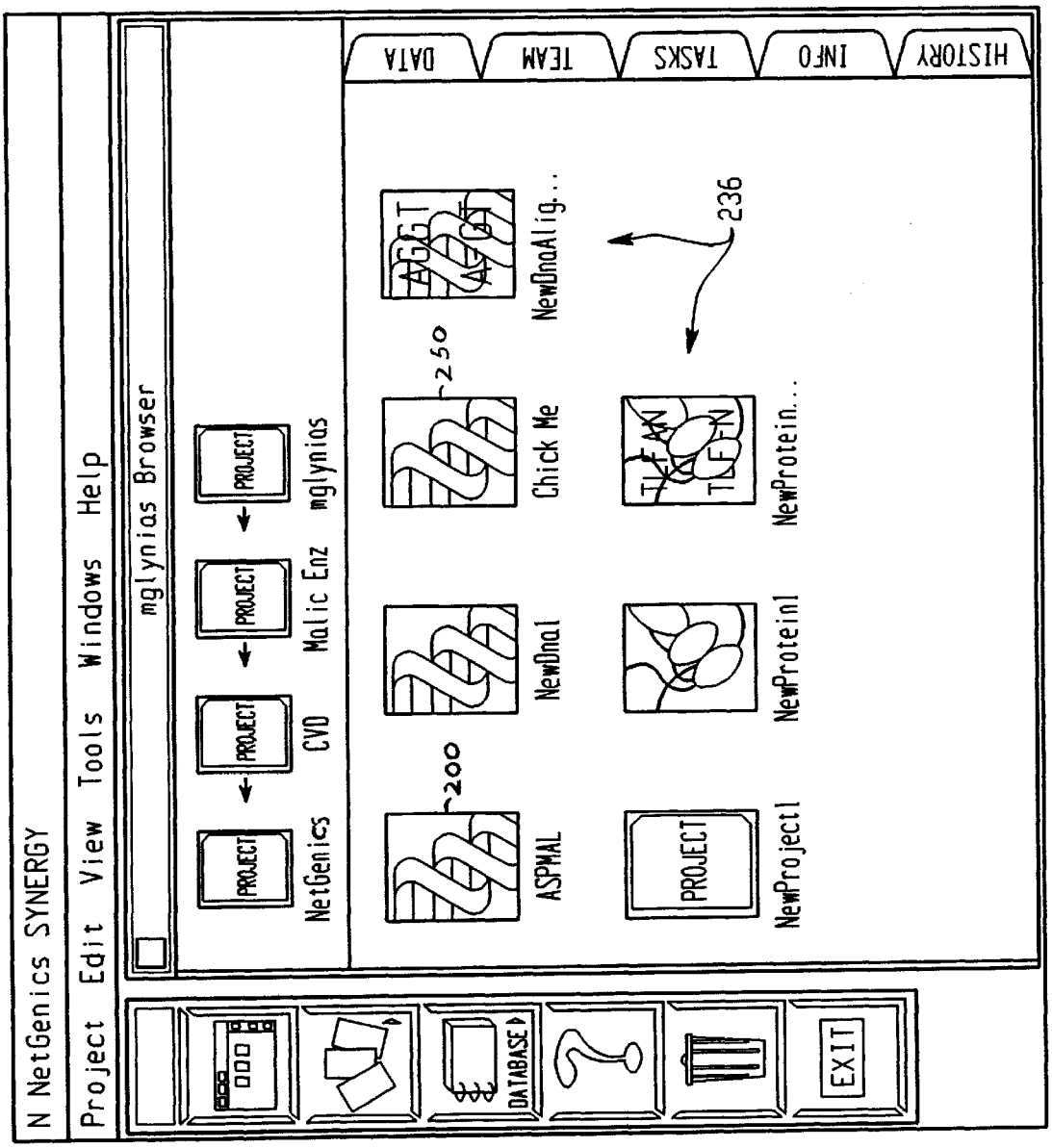
FIG. 6a is a drawing of one screen view at a client end in accordance with the present invention.
Figure 6B:
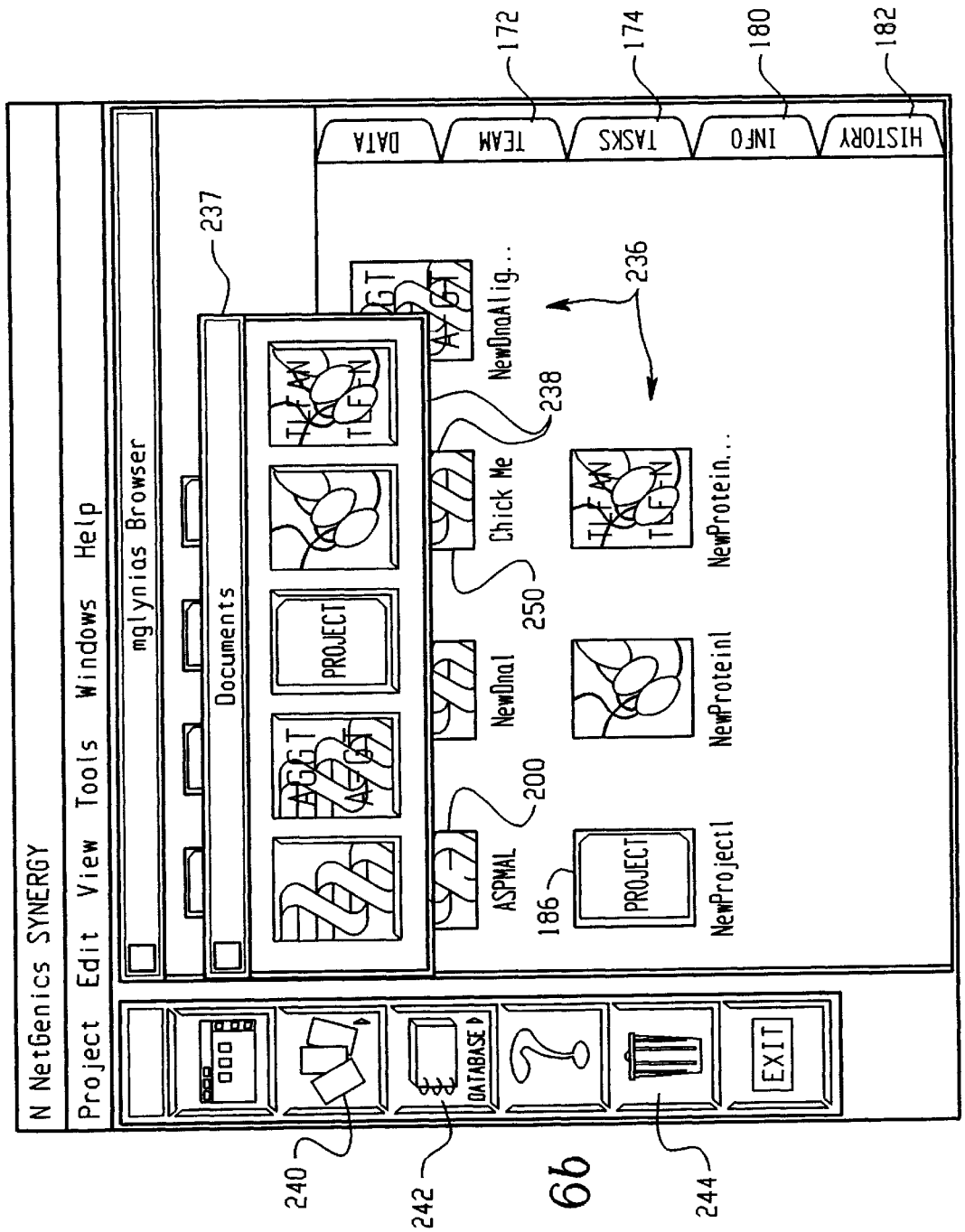
FIG. 6b is another drawing of one screen view at a client end in accordance with the present invention.

For example, if a user wants to create a new DNA item, the user can click on an icon 236 on a screen such as shown in FIGS. 6a and 6b. After the user has authenticated to the system 100 via the session manager 120, the workstation client calls the dictionary 117 server and requests a list of all the data objects the system knows how to manage or create. The list is used to build a document toolbar 237 which displays icons representing all of the items for which item factories exist and are registered with the project manager 116. The list used to build the document toolbar 237 includes an image of an icon and the names of Java classes that can implement the respective data types Should a user wish to create a new Human Alcohol Dehydrogenase DNA sequence object having the following sequence:

```
  1 gaagacagaa tcaacatgag cacagcagga aaagtaatca aatgcaaagc
    agctgtgcta
 61 tgggagttaa agaaaccctt ttccattgag gaggtggagg ttgcacctcc taaggcccat
121 gaagttcgta ttaagatggt ggctgtagga atctgtggca cagatgacca cgtggttagt
181 ggtaccatgg tgaccccact tcctgtgatt ttaggccatg aggcagccgg catcgtggag
241 agtgttggag aaggggtgac tacagtcaaa ccaggtgata aagtcatccc actcgctatt
301 cctcagtgtg gaaaatgcag aatttgtaaa aacccggaga gcaactactg
    cttgaaaaac
361 gatgtaagca atcctcaggg gaccctgcag gatggcacca gcaggttcac
    ctgcaggagg
421 aagcccatcc accacttcct tggcatcagc accttctcac agtacacagt ggtggatgaa
481 aatgcagtag ccaaaattga tgcagcctcg cctctagaga aagtctgtct cattggctgt
541 ggattttcaa ctggttatgg gtctgcagtc aatgttgcca aggtcacccc
    aggctctacc
601 tgtgctgtgt ttggcctggg aggggtcggc ctatctgcta ttatgggctg
    taaagcagct
661 ggggcagcca gaatcattgc ggtggacatc aacaaggaca aatttgcaaa
    ggccaaagag
721 ttgggggcca ctgaatgcat caaccctcaa gactacaaga aacccatcca ggaggtgcta
781 aaggaaatga ctgatggagg tgtggatttt tcatttgaag tcatcggtcg gcttgacacc
841 atgatggctt ccctgttatg ttgtcatgag gcatgtggca caagtgtcat cgtaggggta
901 cctcctgatt cccaaaacct ctcaatgaac cctatgctgc tactgactgg acgtacctgg
961 aagggagcta ttcttggtgg ctttaaaagt aaagaatgtg tcccaaaact tgtggctgat
1021 tttatggcta agaagttttc attggatgca ttaataaccc atgttttacc ttttgaaaaa
1081 ataaatgaag gatttgacct gcttcactct gggaaaagta tccgtaccat tctgatgttt
1141 tgagacaata cagatgtttt cccttgtggc agtcttcagc ctcctctacc ctacatgatc
1201 tggagcaaca gctgggaaat atcattaatt ctgctcatca cagattttat caataaatta
1261 catttggggg cttccaaag aaatggaaat tgatgtaaaa ttatttttca agcaaatgtt
1321 taaaatccaa atgagaacta aataaagtgt tgaacatcag ctggggaatt gaagccaata
1381 aaccttcctt cttaaccatt
```

The user would request a new DNA sequence object by mouse-clicking on the DNA object icon 238 on the document toolbar 237. The client does this by invoking a method on the current project as shown:

aProject.NewItem ("Sequences:DNA Sequence")

The "aProject" object in the client 110 is a client 110 stub proxy that represents a server side project implemented by the project manager 116. The project manager 116 consults the list of available item factories and selects a factory object that is registered to handle creation of DNA sequence objects. The factory (in this case a sequence item factory) completes the creation of the sequence item requested and returns it to the project manager 116. The project manager 116 then returns the new reference to the requesting client 110 and notifies all other interested clients 110 that a new item has been created by sending a callback. The client 110 will use the new returned reference to the sequence object to initialize a local proxy object that communicates with the DNA Sequence implementation object implemented on the server. The user may then populate the contents of the new DNA sequence item by making method calls using the client 110 stub proxy. A specific case of this would include pasting the residues (shown above) into the newly created DNA sequence.

All users actively viewing a project (Project team members as described below) will have registered with the server 112 stub representing that project to receive callbacks upon state changes. When a callback is received from the server, all registered clients 110 refresh the state of the project being viewed by using a GetContents command (e.g., aProject.GetContents). The client 110 project would be updated with the newly-created DNA sequence object. The server 112 provides the following information to the clients 110:

| ObjRef | Class | Date | Image | Name | Creator |
|---|---|---|---|---|---|
| Sequence-Item | DNA Sequence | 1-1-97 | DNAIcon.jpg | ADH_Human | Joe User |

In this instance, "Class" associates the new objects type with a set of Java view classes resident on the client 110 using the information in the document toolbar 237 (described above). The client 110 is aware, through the downloaded Java classes using instantiation by name (described below) of the properties and methods of that class. The client 110 creates the ADH_Human instance of the DNA sequence object using Java instantiation by name:

Class myclass=Class.ForName ("DNA")

DNA myDNA=myclass.newInstance ("ADH_Human")

Opening an existing item . . .

In another specific example of the invention, should a user wish to view a DNA sequence object containing the data relevant for the DNA sequence of duck malic Enzyme (ASPMAL), the user would mouse-click on the icon bearing the name ASPMAL (200 in FIG. 6a). When the ASPMAL icon 200 is clicked, the client 110 requests from the project manager 116 the specific data in the datastore 140 for the duck malic enzyme item. The project manager 116 via the data manger 126 then locates the information contained in the data store 140 or the data store of a sub-server (e.g., other client). The project manager 116 then returns a reference to the data object, allowing the client 110 to interact directly with the data manager 126 to view the object-specific data associated with the duck malic enzyme object.

Figure 7B:
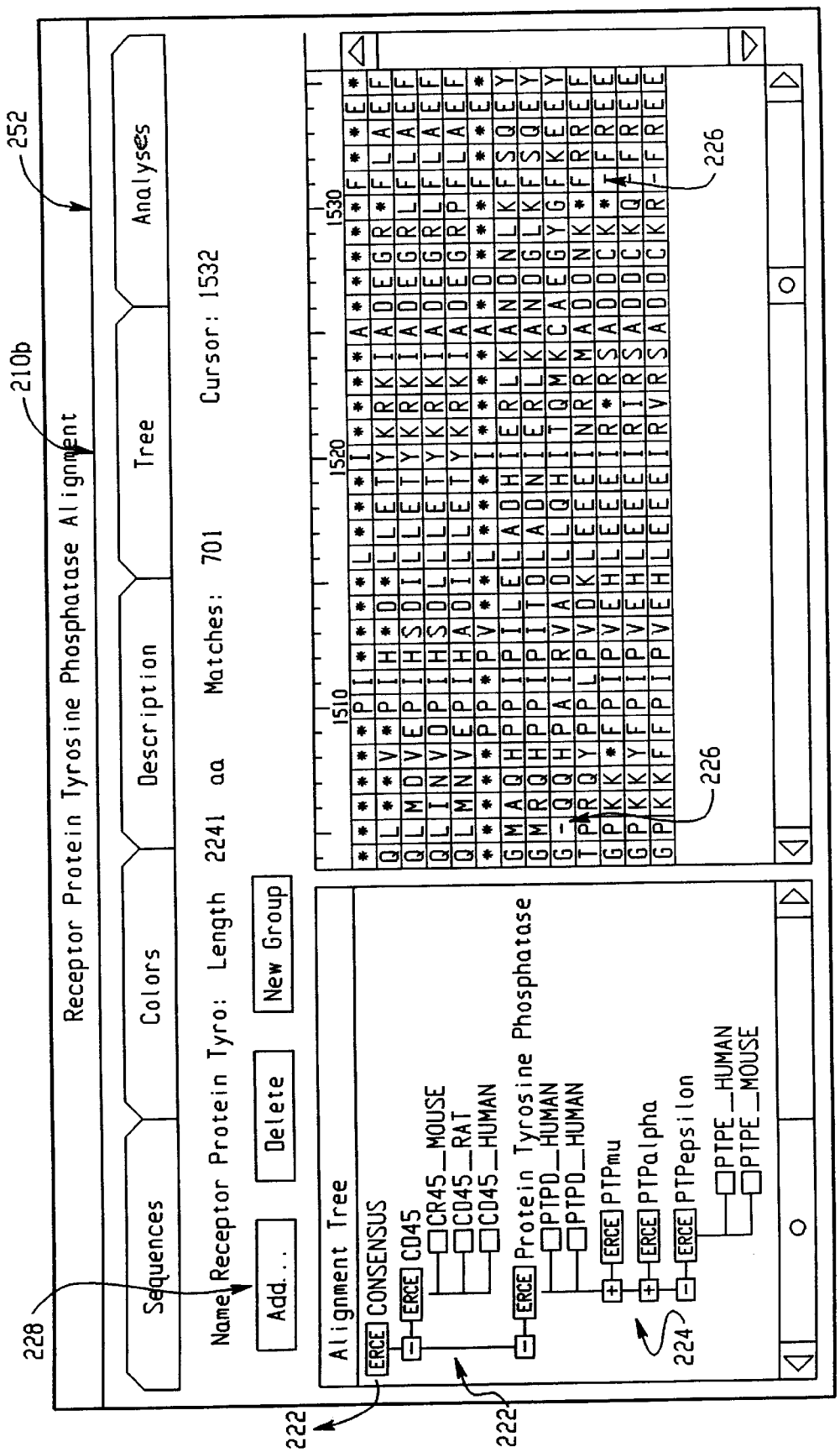
FIG. 7b is another drawing of a screen view for viewing DNA sequence data in accordance with the present invention.
Figure 7C:
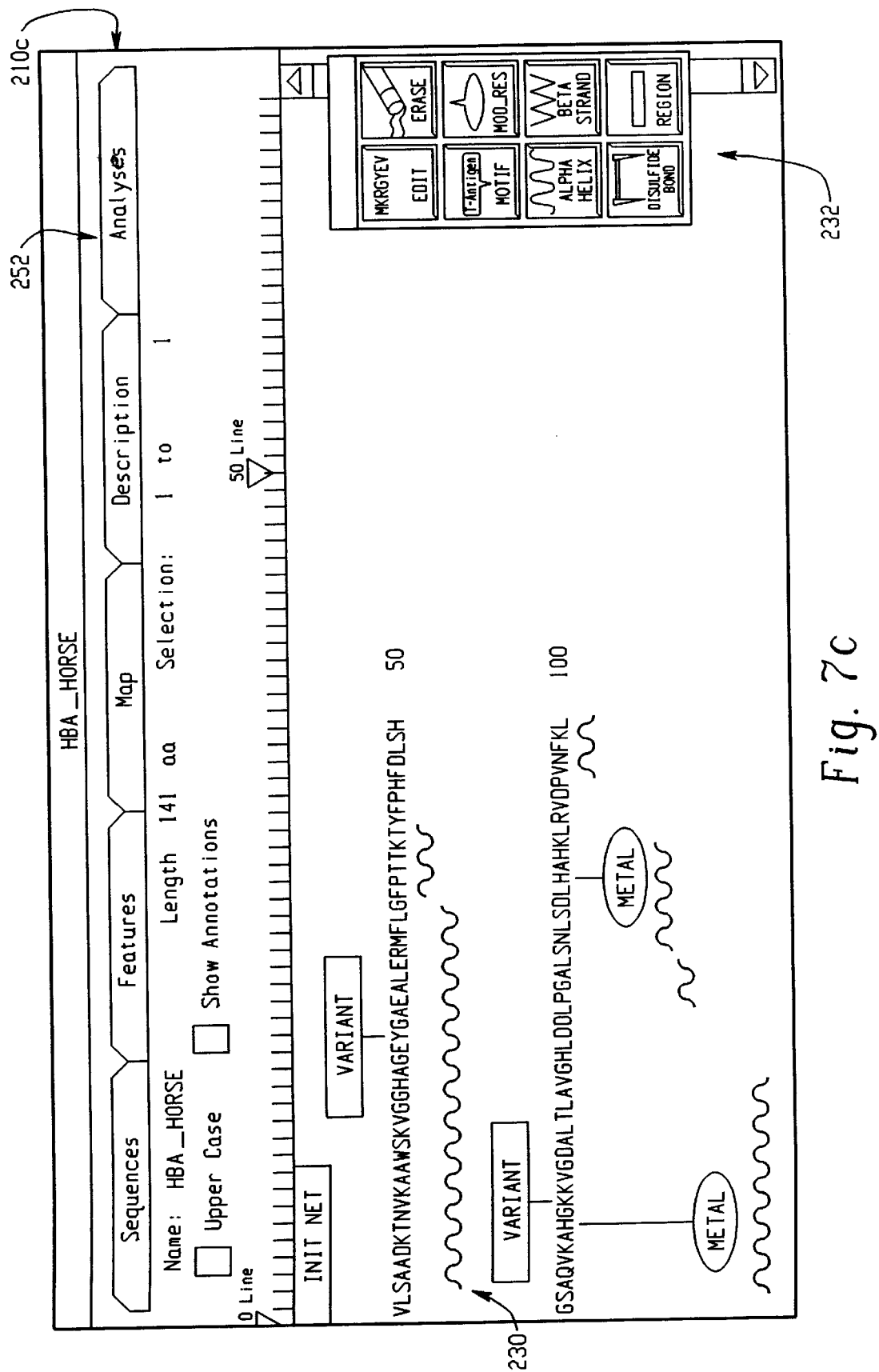
FIG. 7c is another drawing of a screen view for viewing DNA sequence data in accordance with the present invention.

Once the ASPMAL icon 200 is selected by the user, the screen 210 shown in FIG. 7a appears. This screen 210 represents all of the data representing the duck malic enzyme that is known thus far to the project. The user can also pull up more than one of the tab functions as the screen 210b shown in FIG. 7b illustrates. Sequences can be dragged out 220, collected 222, or structured and organized to facilitate comparisons between groups 224. Sequences can also be edited by simple click-and-drag 226, or added 228. Annotations 230 can also be imported as the screen 210c shown in FIG. 7c illustrates. Manual annotation using a tool palette 232 is also permissible.

The user has the ability to call specialized methods on the ASPMAL sequence object (or any other analyzable object). These methods are generally referred to as analyses. The analysis tab 252 (FIG. 7c) provides access to all of the DNA sequence analysis tools, as well as the saved results of analyses previously carried out on this sequence. All these results are permanently archived by the present invention, allowing the user to view the full history of the method called on a DNA sequence object, thus allowing the user, or any member of the project team, to have immediate access to all the data and all the analyses on this data. The mechanics of running the actual programs that perform these analyses are transparent to the user.

For example, a user may desire to perform an analysis on the Chick Malic Enzyme. The user would simply select (e.g., click the Chick Malic Enzyme (Chick ME) Protein Item; icon 250 (FIG. 6a)) and then double click the Malic Enzyme (Chick ME) Protein icon 250 to view a screen similar to that shown in FIG. 7a except that it would relate to the data for chick Malic enzyme.

Figure 8A:
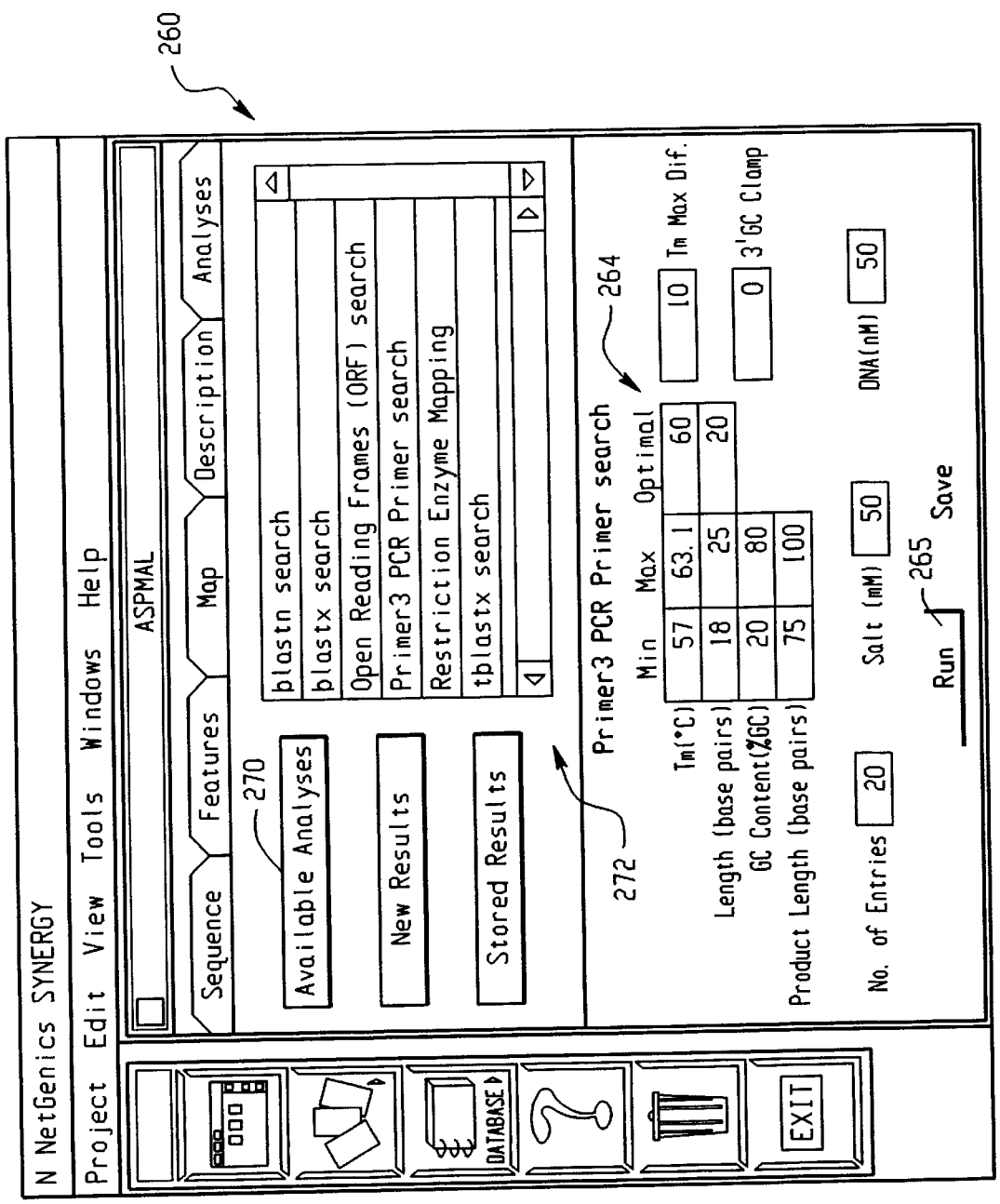
FIG. 8a is a drawing of a screen view of a data function in accordance with the present invention.

The user by selecting the analyses tab 252 (FIGS. 7b, 7c) displays the screen 260 shown in FIG. 8a. The user could select among the various analyses tools available for the chick Malic enzyme. The user may then enter various parameters relating to the chick Malic enzyme in the parameter fields 264. The available analyses list 270 provides for performing the following analyses: (1) Find PCR parameters; (2) Blast vs. DNA database; (3) Blast vs. Protein Database; and (4) Blast vs. TransDNA Database. Additionally, there is an analysis results view 272 that allows the user to view the results of any of the analyses that have already been performed or of any stored analyses. It should be appreciated that although only a few types of analyses were discussed, it will be appreciated that any suitable number of analyses and related contents of the analyses may be employed to carry out the present invention.

In order to determine and render the list of available analyses 270 the client 110 requests from the analysis manager 130 a list of analyses that know how to operate upon the given data type. For instance, a displayed DNA sequence would return a list of available analyses corresponding specifically to DNA. Protein sequences would return a different list of analysis corresponding specifically to protein sequence objects.

Figure 8B:
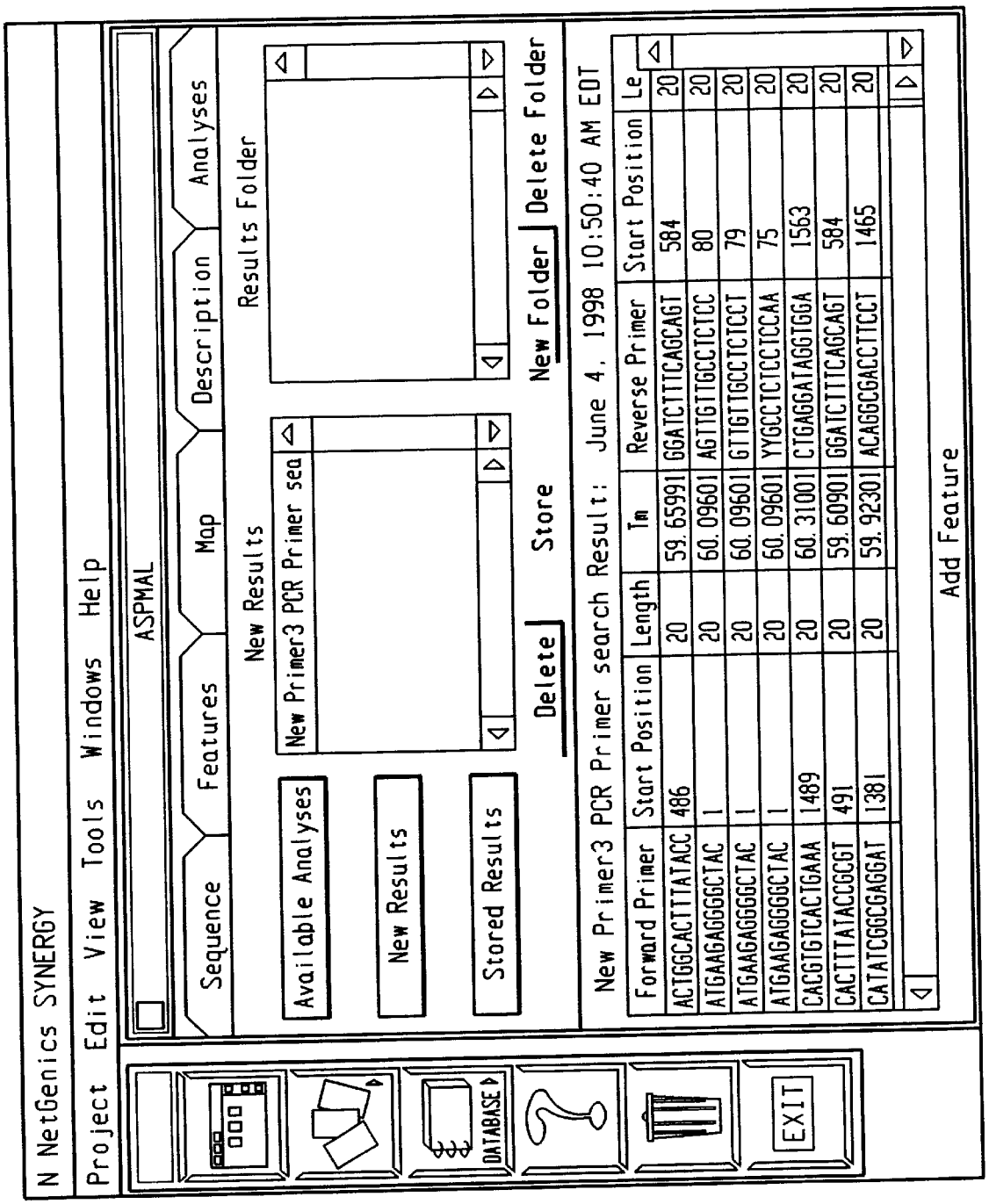
FIG. 8b is a drawing of a screen view of an analysis results function in accordance with the present invention.

For example, in FIG. 8a upon selecting "Find PCR Primers" from the list of available analyses 270 the user would be presented with a parameters view 264 that is instantiated by name through a lookup operation on a dictionary that implements mappings between analysis names and corresponding Java view classes. The user would then complete the view by specifying the input parameters that are to be applied to the analysis. Upon selecting the "Run" button 265 on the parameters view 264 the client communicates the parameters as well as the name of the analysis to the analysis manager 130 which queues it for execution to the analysis queue runner 132. Upon completion of the queued analysis the newly created analysis result is added to the data object's list of analysis results as shown in FIG. 8b. The registered clients 110 are notified of the new analysis result via a callback.

Figure 6C:
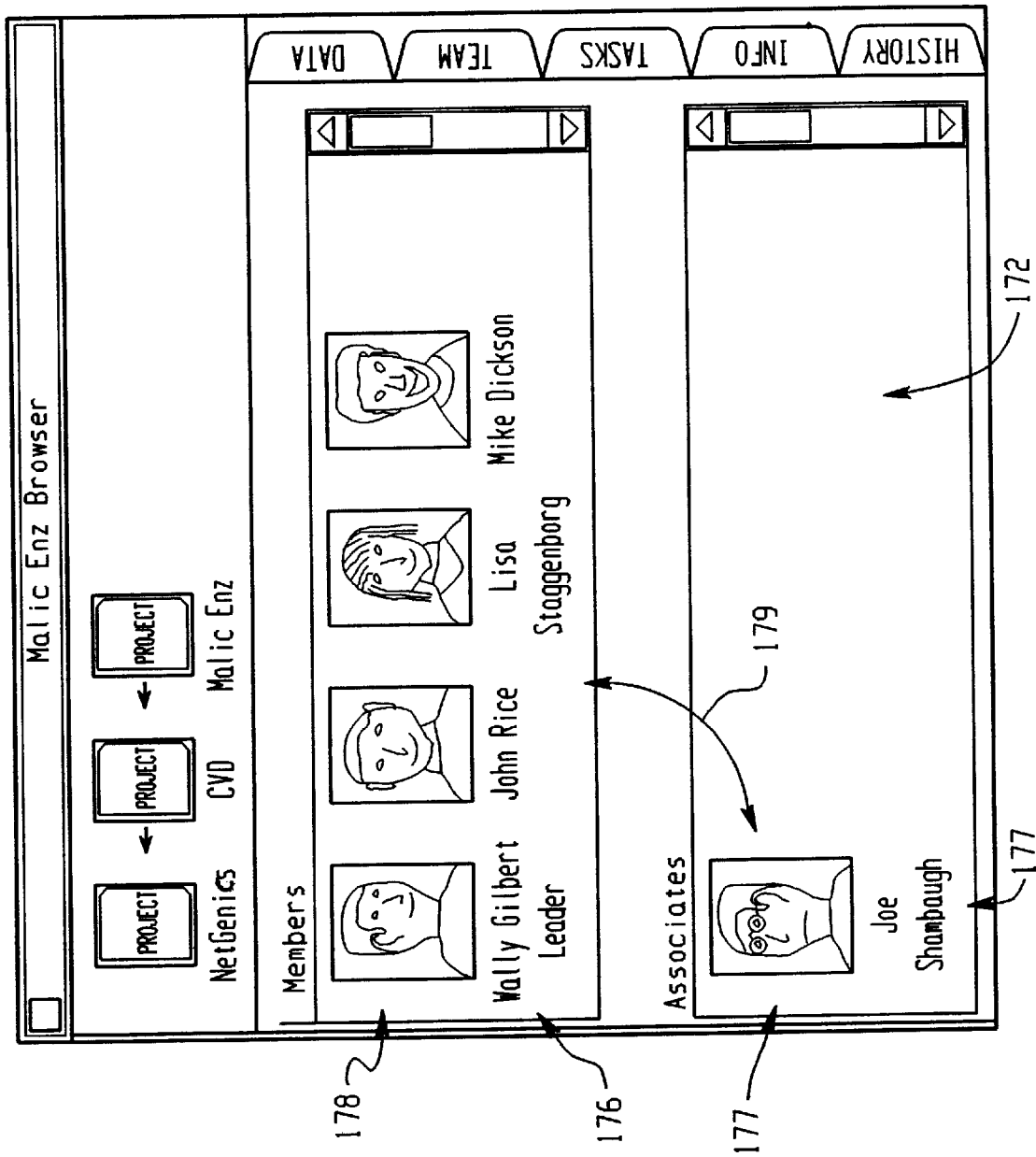
FIG. 6c is another drawing of one screen view at a client end in accordance with the present invention.

Referring to FIGS. 6b & 6c the project also includes a team (which are the people who can actually operate on the contents of the screen), members 176 of the team being displayed by clicking the team tab 172, as illustrated by FIG. 6b. The team may be divided into members 176 and associates 177 with the members 176 having read-write access while the associates 177 only having read access to the data in connection with the project. Additionally, the team has a team leader 178, who also has read-write access to data but additionally has control over team membership 179. The tasks tab 174 is a project manager function which when clicked provides a software manager similar to Microsoft Project. The info tab 180 when clicked provides text that describes the subject DNA item. The history tab 182 when clicked lists the history of every kind of change ever done on any item in the subject project. Thus the history is generally an audit trail for the project.

In another example, the user can select a different project 186 on a screen such as shown in FIG. 6b. The user can call the project manager and request a different list relating to molecular structures, receiving a different screen. Again, the new screen will comprise several icons 236 with different tab functions 172, 174, 180, 182. Depending on the project screen, different data could be accessed. As illustrated in FIG. 6b, the screen might allow the user to access all available data types 240, multiple databases of different formats 242, or all previously saved data 244.

It will be appreciated that a variety of servers, data managers, project managers, etc. could be employed in connection with the present invention all which fall within the scope of the invention. Moreover, it is to be appreciated that a first computer may act as a client to a second computer in one instance, and act as a server to the second computer in another instance. Furthermore, the present invention may provide for a system including a plurality of computers wherein any one of the plurality of computers may dynamically assume any of a plurality of functions carried out by at least one of the other computers.

Thus, the present invention employs the ability of a CORBA call to return a string, where that string is the name of a Java class, in order to perform Java class instantiation by name. Furthermore, these classes are downloaded in real-time unlike some conventional systems where the classes are bound into an image. As is discussed in greater detail herein, the employment of Java provides for a platform independent system, and a substantially dynamic system whereas conventional systems are not platform independent nor dynamic.

As discussed above, the dynamic nature of the present system provides for the addition of new data contents in real-time, and through the callback mechanism the view at the client end would be immediately refreshed and redisplayed with the new data. As a result research in connection with bioinformatics and/or chemical informatics is greatly facilitated by the present invention.

Figure 9:
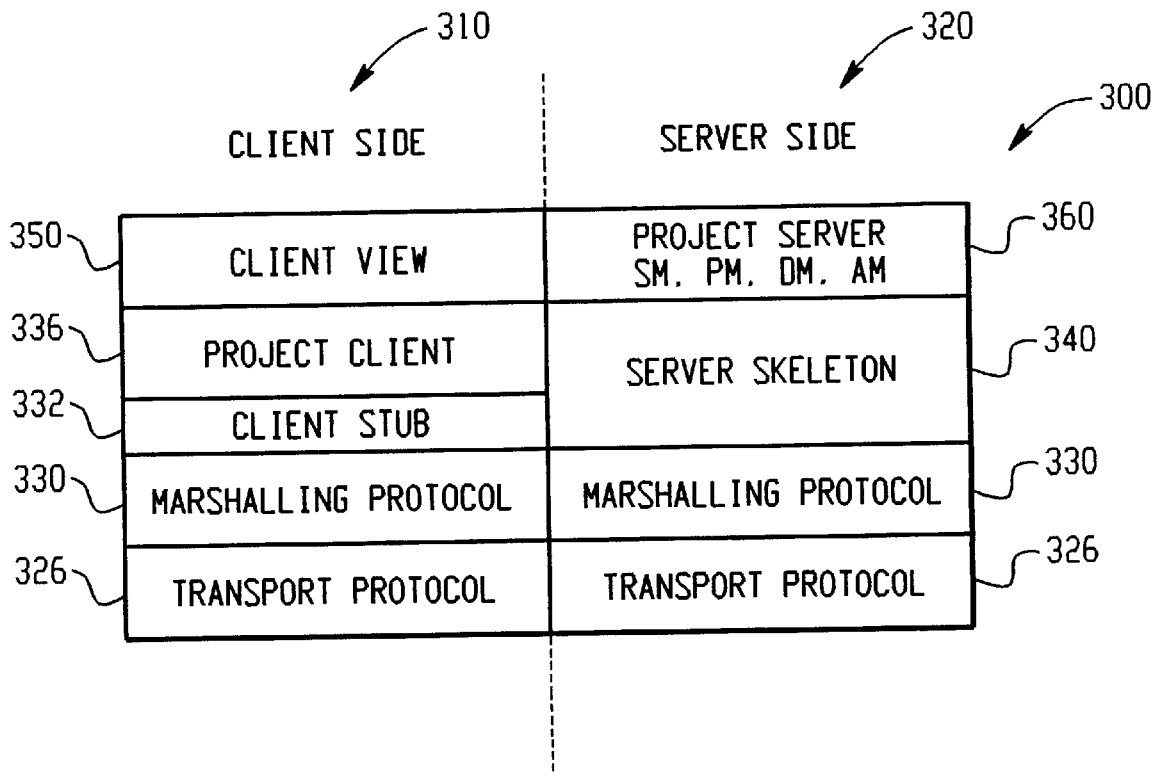
FIG. 9 is a diagram representative of the network architectural layering of the system in accordance with the present invention.

FIG. 9 is a drawing depicting a network architecture 300 according to one aspect of the present invention. It will be appreciated that various architectures may be employed to carry out the present invention, all which fall within the scope of the present invention. The architecture 300 consists of several network layers. The architecture 300 is divided up to show the architecture on the client side 310 and the architecture on the server side 320. The bottom layer 326 is the transport protocol layer. In the preferred embodiment, the transport protocol layer 326 is a TCP/IP layer—of course any suitable type of transport protocol layer may be employed to carry out the present invention. The transport protocol layer 326 exists on both the client side 310 and the server side 320. This layer 326 in general serves to transport data without error or loss.

On top of the transport layer 326 is a marshaling protocol layer 330 on both the client side 310 and server side 320. In this embodiment, the marshaling protocol layer 310 is IIOP (Internet Interoperation Protocol). The marshaling protocol layer 320 provides for connecting client objects with server objects. On the client side 310, over the marshaling protocol layer 330 is a client stub 332 which provides for gluing the project client 336 to the marshaling protocol layer 330, and it also provides for connecting the project client 336 to the server skeleton 340. The project client 336 serves to manage projects on the client side 310 for a particular client 110. The project client's 336 preferred implementation is Java, however, it should be appreciated that other programming languages could be used for the proj. client 336. In general, the proj. client 336 is a cached copy of a corresponding project stored on the server 112. On top of the proj. client 336 is a client view layer 350 which provides for viewing data and analysis in general.

The CORBA 332 stub (written in Java) and the view manager 350 are downloaded at run time to create the client object class which is used to instantiate new objects in the server 112.

Moving to the server side 320, on top of the marshaling protocol layer 330 is a server skeleton 340 which provides for connecting to the requested objects from the clients 110 to server 112. Thus, the server skeleton 340 provides for the brokering aspect of the system 100 wherein objects can be requested and delivered to a plurality of clients 110 having different platforms. Furthermore, this layer 340 provides for doing the same among a plurality of servers 112 in the system 100. The server stub 340 connects the marshaling protocol layer 330 to the project server layer 360. The project server layer 360 includes the project manager 116, the data manager 126 and the analysis manager 130.

The project server layer 360 provides for the creation and maintenance of projects within the system 100. As is discussed in greater detail above, the project manager 116 controls the flow of objects (e.g., data objects and analyses objects) within the system 100. The project server layer 360 also includes the data manager 126 for creating and maintaining data objects for each project and the analyses manager 130. As noted above, the analysis manager 130 serves to create and maintain analyses objects for analyzing the data objects which were generated by the data manager 126.

As indicated above, it will be appreciated that various architectures may be employed to carry out the present invention, all which fall within the scope of the present invention. Although the two parallel frameworks (the framework on the server side, and the one on the client side) appear similar, the two frameworks are complimentary rather than cloned. Data content on the client side does not need to be an exact duplicate of the data content on the server side, due to the dynamic application access discussed above. Tasks are completed more effectively as the users can define what they want to see and what they want to do, and have the tasks completed "just-in-time". Zero footprint clients and the separation of the client 110 and the server 112 through the analysis manager 130 and the project manager 116 allow effective data and information delivery and interaction.

Because the client is informed of how to handle representations of DNA sequences, it is capable of drawing the properties of the object. In the absence of the present invention, the actions involved in running many analyses (such as the BLAST homology search described below) would require significantly more effort on the part of the user. In this example, a typical BLAST homology search would consist of seven steps:

1. Perform analysis on desktop PC
2. Transfer data to Internet programs
3. Reformat data for BLAST search
4. Remember and set BLAST parameters
5. Interpret BLAST results
6. Manually download each "hit"
7. Convert data back to desktop format However, the present invention provides for accomplishing the above with a two-step process, utilizing the analysis tab 252 (FIG. 7a) as described above. In a similar manner, the client 110 is capable of adding and manipulating specific DNA sequence data, by calling services on the DNA object, with assistance from the server 112. For example, if the client 110 wants to compare DNA sequence with a database, to see if there are similar DNA sequences which have been identified, using a service called BLAST, the client would invoke a method on the DNA sequence object to call the service object "BLAST" on the server 112. This is, again, accomplished through the instantiation of a proxy object "DNA Sequence.ADH_Human.BLAST". The proxy object is again aware of where in the server 112 the service for BLAST is located, and carries with it the parameters (arguments) for the particular DNA object it is serving.

When the proxy object reaches the server 112, it provides the ORB 72 with the location and arguments for the service. The ORB 72 translates those arguments into Method Calls (IDL Stubs) 82 that are understandable by the BLAST service object. The BLAST service performs the analysis and returns the output to the ORB 72, which then translates the output so that it is understandable to the client 110. Once again, the server 112 performs a callback to all interested clients, which then update their contents with the aProject.GetContents command. The BLAST results are communicated to all of the clients 110, simultaneously.

According to another aspect of the invention, an example of the present invention being applied to the area of chemiinformatics is described below. In this instance, a client 110 desires to create a new chemical structure object, which can be employed to query various databases. The user would request a new chemical structure object by mouse-clicking on the chemical structure object icon on the document toolbar 237 (FIG. 6b). The client does this by invoking a method on the current project as shown:

aProject.NewItem ("Structures:Chem Structure")

Figure 10:
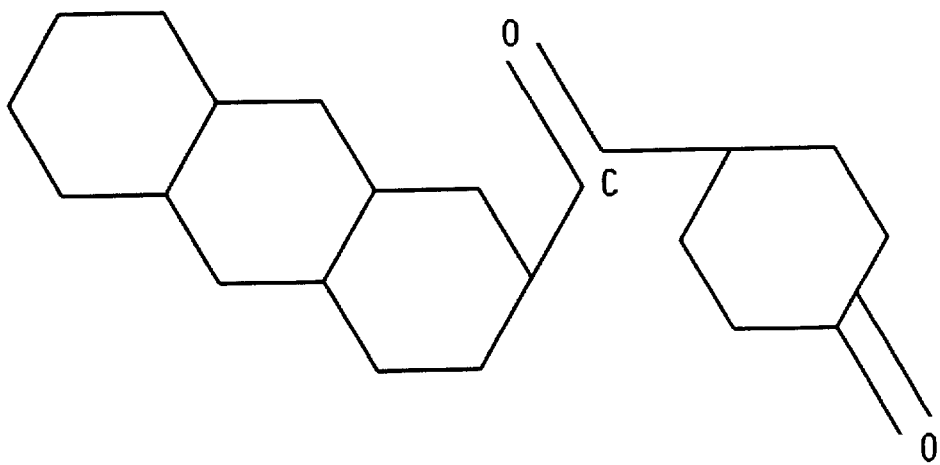
FIG. 10 is a drawing of an object representing a chemical structure in accordance with the present invention.

The "aProject" object in the client 110 is a client 110 stub proxy that represents a server side project implemented by the project manager 116. The project manager 116 consults the list of available item factories and selects a factory object that registered to handle creation of chemical structure objects. The factory (in this case a structure item factory) completes the creation of the structure item requested and returns it to the project manager 116. The project manager 116 then returns the new reference to the requesting client 110 and notifies all other interested clients 110 that a new item has been created by sending a callback. The client 110 will use the new returned reference to the sequence object to initialize a local proxy object that communicates with the Chem.Structure Sequence implementation object implemented on the server. The user may then populate the contents of the new chemical structure item by making method calls using the client 110 stub proxy. A specific case of this would include pasting the chemical structure (shown in FIG. 10) into the newly created Chem.Structure.

All users actively viewing a project (Project team members as described above) will have registered with the server 112 stub representing that the project is to receive callbacks upon state changes. When a callback is received from the server, all registered clients 110 refresh the state of the project being viewed by using a GetContents command (e.g., aProject.GetContents). The client 110 project would be updated with the newly-created chemical structure object. The server 112 provides the following information to the clients 110:

| ObjRef | Class | Date | Image | Name | Creator |
|---|---|---|---|---|---|
| StructureItem | Chem.Structure | 1-1-97 | ChemStrIcon.jpg | Molecule34 | Joe User |

In this instance, "Class" associates the new objects type with a set of Java view classes resident on the client 110 using the information in the document toolbar 237 (described above). The client 110 is aware, through the downloaded Java classes using instantiation by name (described below) of the properties and methods of that class. The client 110 creates the Molecule34 instance of the chemical structure object using Java instantiation by name:

Class myclass=Class.ForName ("Chem")

Chem myChem=myclass.newInstance ("Mollecule34")

In a similar manner, the client 110 is capable of adding and manipulating specific chemical structure data by calling services on the ChemStructure object with the assistance of the server 112 through the process described above. In this example, the user again selects the Analysis Tab 252 from a view of the chemical structure, and the dictionary builds a list of available analyses 270, based on the registered analyses that were appropriate for a chemical structure object. The user then selects an analysis from the list of available analyses 270, and the user is presented with a parameters view 264 that is instantiated by name through a lookup operation on a dictionary that implements mappings between analysis names and corresponding Java view classes. The user then completes the view by specifying the input parameters that are to be applied to the analysis. This again is accomplished through the instantiation of a proxy object (in this case, "ChemStructure.StructureQuery"). Upon selecting the "Run" button on the parameters view 264 the client communicates the parameters as well as the name of the analysis to the analysis manager 130 which queues it for execution to the analysis queue runner 132. Upon completion of the queued analysis the newly created analysis result is added to the data object's list of analysis results registered clients 110 are notified of the new analysis result via a callback.

The output from this Structure Query search may be used to access particular information regarding the function of this molecule, which can then be analyzed against other structure types, using a function prediction service, for example. This service may be accessed in much the same way as the StructureQuery service.

In most or many cases, the services may be substituted while the client 110 is off-line and then re-loaded by name at run time when the client 110 re-connects. Likewise, all the item classes may be changed, and re-loaded at run time, along with the name and Icon references for each. In this way, the nature and identities of data managers 126 and services can be ignorant to the client 110, and the server 112 can provide the client 110 with the appropriate information for both creation and manipulation of data at log in.

The present invention also provides for inherent collaboration models which support the function and communication style of a particular object. This is accomplished by implementing a "groupware" framework around CORBA where the client 110 is extensible in real time and downloaded as group of Java programs. Such collaboration models may include: screen sharing; annotation merging; document merging, etc.

The three aforementioned collaborative models provide users access to objects in different ways. In particular, through the screen sharing collaborative model, users may view objects in real time. In the annotation or document merging models, a user may contemporaneously access different portions of an object. The screen sharing collaborative model displays all objects within a place that exist on a host station to a number of users on other workstations. However, all objects existing on workstations other than a host will not be displayed until moved to the host. Thus, in the screen sharing collaborative model all users view the same view of an object.

The screen sharing can support different types of interaction among different objects. For example, with a work team of several biotech researchers, a DNA sequence can be analyzed and modified in real-time even though each researcher is at a different location. Furthermore, the screen sharing collaborative model could support shared white boards for notes and instructions, telephony, interactive screen sharing etc. Returning back to the DNA sequence research team, each researcher would posses the ability to modify the sequence.

Objects that can be annotated or merged such as a biology or chemical research document may be opened by all researchers for viewing. However, the view of each user with respect to the research document may be different. As a result several users may access and write to a document simultaneously since no two users have both read and write access to the same portion of the document. Thus, large scale research and collaborative efforts is facilitated by allowing many people on a research team to view and possibly manipulate an object such as a DNA sequence and then together produce a research paper at high speed with a significant reduction in errors since no user can overwrite or modify a portion of a document that is assigned to another.

Furthermore, it will be appreciated that a hybrid shared screen and annotated collaborative framework may be employed. For example, it may be desired that every possible user not be locked out for minor editing where the editing is simply an addition of an annotation. Adding such an annotation may not change the contents of any relevant data so that analyses performed on the particular data may still be valid even with the addition of the annotation. Thus, the hybrid collaborative framework is conducive to DNA research since it is not often that users edit the DNA sequence itself but rather simply annotate the sequence. Of course, some level of locking could be employed to prevent two annotations from conflicting with each other. Any suitable locking scheme may be employed to carry out the present invention. However, in the preferred embodiment, a user holding a lock to portions of a project will release the lock upon logging off the system 100.

For added flexibility, the project can be grouped into super projects and private sub-projects where the data can be drawn and used by an individual for a period of time in his/her own private sub-project and then pull this information into the super project after the individual research has been completed.

Since a drug discovery project is composed of the project data, the project team, the work still to be done, as well as the history of what the team has already accomplished, all of this information about a project is available through a single window on the computer screen. Here a user can view all the data in this project, create new data objects (e.g. DNA or protein objects) or sub-projects, be alerted to new results in collaborative projects, communicate with team members, check the history of the project, or its current task list. Access to the various kinds of data is controlled through the "tabs" on the right edge of the window, e.g. the DATA tab allows the user to view and manipulate project data, while the TEAM tab shows the members and associates of the team.

Any user viewing the contents of a project could be notified immediately whenever any other team member adds to or modifies the data of a project. Access to data in a project is controlled, so that team members have read/write permissions while team associates have read-only permissions. Team members can have private sub-projects, where initial analyses can be conducted. When new data has been validated, it can be shared with the rest of the project team using a simple drag-and-drop operation.

The present invention provides for a collaborative framework model which aids a user in conducting bioinformatics and chemi-informatics research. To this end, the present invention allows users to enter and edit DNA and protein sequences, to analyze and annotate these sequences, to search DNA and protein sequence databases by a number of criteria, to build custom databases, to align sequences, and to perform phylogenetic analysis on these alignments. Additionally, a user may perform creation and analysis of chemical data objects, search these molecules versus structure libraries, investigate interactions between chemical and biological molecules, etc.

On returning information on a sequence to the user, the system 100 parses all cross-references to material stored on other databases. Thus cross-references, abstracts, other sequences and three-dimensional structures are only a mouse-click away. This cross-referencing can provide links to both public and private databases enabling one to immediately access information spread across many unrelated databases. The different formats and properties of the databases themselves are handled in a form transparent to the user.

Furthermore, the system 100 is configurable, so that, if a pharmaceutical company has its own proprietary research database, as well as access to databases licensed from other sources, a database search could automatically search all these public and proprietary databases with a common interface.

Through the use of wrappers, as described above, input and output from various programs are always converted to a common format. This allows the results from one analysis to be automatically used as input for further analyses (e.g., the results from a protein database search can be automatically entered into a multiple sequence alignment).

Not only does this cross-referencing capability serve to create, on the fly, links to internal databases, but it can also be used to alert the user to the fact that specific information passing through the server is of interest to the company in other connections. For example, when different projects intersect, as when a search returns a gene sequence that is already involved in another project at the company, a message, enables immediate access to this information, (or, depending on security concerns, at least the ability to send electronic mail to the other party involved). In a large pharmaceutical company, spread over many sites, perhaps over many continents, there is often no way to detect the convergence of research projects, especially at an early stage. The present invention solves this communication problem and thereby catalyzes collaborations between research groups within the company.

Although the present invention has been described with applications directed to the bioinformatics and/or chemiinformatics arena, it will be appreciated that the present invention may be applied to a variety of vertical markets. For example, the present invention may be employed in a vertical market such as the financial arena where large amounts of financial data are worked with. Thus, substantially any vertical market that is data intensive may employ the present invention to facilitate the handling of data in that market. The scope of the present invention is intended to include the application of the present invention to such markets.

The present invention includes all such equivalents and modifications, and is limited only by the scope of the following claims.

What is claimed is:

1. A framework to facilitate at least one of bioinformatics and chemi-informatics research, comprising:

a plurality of computers, at least one of the plurality of computers running a multi-platform object oriented programming code, and at least one of the plurality of computers storing at least one of biological and chemical data, the computer storing the data providing the computer running the object oriented programming code with program data at run time to enable at least one of creation, manipulation, and viewing of the data, at least one of the plurality of computers being operative as a server, the server providing to the computer running the object oriented programming code a list at run time identifying services available to the server, the list representing objects by class name and the computer running the object oriented programming code being operable to invoke at least one of the services by class name based on the list, thereby causing the server to instantiate corresponding class objects by name at run time; and a network architecture interconnecting the plurality of computers, the network architecture allowing objects to transparently communicate with each other;

whereby the framework provides for integrating and organizing the data to facilitate at least one of biological and chemical research.

2. The framework of claim 1, further comprising means for dynamically swapping operations performed by the computer storing the data with operations performed by the computer running the object oriented programming code.

3. The framework of claim 1, wherein the computer storing the data is operable as the server for the framework.

4. The framework of claim 3, wherein the classes are Java client classes having objects that are instantiated by name at run time to implement Common Object Request Broker Architecture client interfaces to changing server components.

5. The framework of claim 1, wherein the framework organizes the data to perform DNA sequence analysis.

6. The framework of claim 1, wherein the framework organizes the data to perform chemical analysis.

7. The framework of claim 1, wherein a groupware framework is provided around a distributed object model wherein a client is extensible in real time and downloads as a client object.

8. The framework of claim 7, wherein the groupware framework further comprises an annotated collaborative framework, wherein at least two users can concurrently work on different portions of a document object in real-time.

9. The framework of claim 6, wherein the groupware framework further comprises a screen sharing collaborative framework, wherein at least two users of the can concurrently screen share an instance of an object in real-time, the instance of the object running on one of the plurality computers.

10. The framework of claim 7, wherein the groupware framework further comprises an annotated collaborative framework in which at least two users of the system can concurrently work on different portions of a document object in real-time.

11. The framework of claim 10, wherein each user sharing the document object in the collaborative framework is dynamically assigned different portions of the document object so as to inhibit multiple users from concurrently modifying the same portion of the document object.

12. The framework of claim 1, wherein the server provides the computer running the object oriented programming code with an updated list of objects to reflect a change to the list of objects available to the server.

13. A framework to facilitate research, comprising:

at least two computers, including a first computer and a second computer, the first computer running multi-platform object oriented programming code and storing vertical market data, the first computer providing to the second computer a list at run time, the list identifying by class name services available to the first computer, the second computer being operable to invoke at least one of the services by class name based on the list causing the first computer to instantiate corresponding class objects by class name at run time; and a network architecture operatively coupling the at least two computers, the network architecture allowing objects to transparently communicate with each other and affording the second computer access to the object oriented programming code and the stored data;

whereby the framework provides for integrating and organizing the data to facilitate research wherein the framework organizes the data to perform DNA sequence analysis.

14. An informatics research system, comprising:

a server computer for carrying out operations in connection with the system, the server computer being operatively coupled to a network backbone;

at least one client computer for providing user access to the informatics research system, the at least one client computer being operatively coupled to the network backbone; and the client computer having zero footprint access to a plurality of software applications and informatics data via the server computer, and the server sending the at least one client computer a list at run time identifying services available to the server computer, the list representing class objects by class name and the client computer being operable to invoke a service by class name based on the list and cause the server to instantiate a corresponding class object by name at run time;

the client computer including item classes which represent views of data residing on the server computer, the item classes including a DNA sequence item, and the client computer serving as a view manager of persistent data residing on the server computer.

* * * * *